United States Patent
Eren et al.

(10) Patent No.: US 8,673,270 B2
(45) Date of Patent: Mar. 18, 2014

(54) RGD-CONTAINING PEPTIDOMIMETICS AND USES THEREOF

(75) Inventors: Doron Eren, Netaim (IL); Tamar Yechezkel, Shoham (IL); Yoseph Salitra, Rehovot (IL); Natalia Koudinova, Rehovot (IL)

(73) Assignee: Steba Biotech S.A., Luxembourg (LU)

( * ) Notice: Subject to any disclaimer, the term of this patent is extended or adjusted under 35 U.S.C. 154(b) by 104 days.

(21) Appl. No.: 13/125,371

(22) PCT Filed: Oct. 22, 2009

(86) PCT No.: PCT/IL2009/000995
§ 371 (c)(1),
(2), (4) Date: Jun. 29, 2011

(87) PCT Pub. No.: WO2010/046900
PCT Pub. Date: Apr. 29, 2010

(65) Prior Publication Data
US 2011/0250144 A1    Oct. 13, 2011

Related U.S. Application Data

(60) Provisional application No. 61/107,952, filed on Oct. 23, 2008.

(51) Int. Cl.
*A61K 49/00* (2006.01)
*A61K 35/00* (2006.01)
*C08G 63/91* (2006.01)
*C07K 5/12* (2006.01)
*C07K 7/56* (2006.01)

(52) U.S. Cl.
USPC ............ 424/9.6; 530/330; 530/329; 530/328; 530/327; 525/54.1; 514/21.4

(58) Field of Classification Search
None
See application file for complete search history.

(56) References Cited

U.S. PATENT DOCUMENTS 5,849,692 A    12/1998    Jonczyk et al.

FOREIGN PATENT DOCUMENTS

WO    WO 9810795 A2    3/1998
WO    WO 2008023378 A1    2/2008

OTHER PUBLICATIONS

Arap, Wadih et al., "Targeting the prostate for destruction through a vascular address", PNAS, vol. 99, No. 3, pp. 1527-1531, (2002).
Arap, Wadih et al., "Cancer Treatment by Targeted Drug Delivery to Tumor Vasculature in a Mouse Model", Science, vol. 279, No. 377, pp. 377-380, (1998).
Assa-Munt, Nuria et al., "Solution Structures and Integrin Binding Activities of an RGD Peptide with Two Isomers", Biochemistry, vol. 40, No. 8, pp. 2373-2378, (2001).
Banfi, Luca et al., "Synthesis and biological evaluation of new conformationally biased integrin ligands based on a tetrahydroazoninone scaffold", Bioorganic & Medicinal Chemistry Letters, vol. 17, pp. 1341-1345, (2007).
Belvisi, Laura et al., "Biological and molecular properties of a new AlphavBeta3/AlphavBeta5 integrin antagonist", Molecular Cancer Therapeutics, vol. 4, pp. 1670-1680, (2005).
Chaleix, Vincent et al., "RGD-Porphyrin Conjugates: Synthesis and Potential Application in Photodynamic Therapy", European Journal of Organic Chemistry, pp. 1486-1493, (2003).
Dijkgraaf, Ingrid et al., "Synthesis and biological evaluation of potent AlphavBeta3-integrin receptor antagonists", Nuclear Medicine and Biology, vol. 33, pp. 953-961, (2006).
Ellerby, Michael H. et al., "Anti-cancer activity of targeted pro-apoptotic peptides", Nature Medicine, vol. 5, No. 9, pp. 1032-1038, (1999).
Goligorsky, Michael S. et al., "Molecular mimicry of integrin ligation: therapeutic potential of arginine-glycine-aspartic acid (RGD) peptides", Nephrology Dialysis Transplantation, vol. 13, pp. 254-263, (1998).
Hardan, I. et al., "Inhibition of metastatic cell colonization in murine lungs and tumor-induced morbidity by non-peptidic arg-gly-asp mimetics", International Journal of Cancer, vol. 55, pp. 1023-1028, (1993).
Haubner, Roland et al., "Noninvasive Imaging of AlphavBeta3 Integrin Expression Using 18F-labeled RGD-containing Glycopeptide and Positron Emission Tomography", Cancer Research, vol. 61, pp. 1781-1785, (2001).
Haubner, Roland et al., "Structural and Functional Aspects of RGD-Containing Cyclic Pentapeptides as Highly Potent and Selective Integrin AlphavBeta3 Antagonists", Journal of the American Chemical Society, vol. 118, pp. 7461-7472, (1996).
Kawaguchi, Michiya et al., "A Novel Synthetic Arg-Gly-Asp-Containing Peptide Cyclo(-RGDf=V-) Is the Potent Inhibitor of Angiogenesis", Biochemical and Biophysical Research Communications, vol. 288, pp. 711-717, (2001).
Lark, Michael W. et al., "Design and Characterization of Orally Active Arg-Gly-Asp Peptidomimetic Vitronectin Receptor Antagonist SB 265123 for Prevention of Bone Loss in Osteoporosis", The Journal of Pharmacology and Experimental Therapeutics, vol. 291, No. 2, pp. 612-617, (1999).

(Continued)

*Primary Examiner* — Cecilia J Tsang
*Assistant Examiner* — Tara Martinez
(74) *Attorney, Agent, or Firm* — Browdy and Neimark, PLLC

(57) ABSTRACT

The invention provides RGD-containing cyclic peptidomimetics; conjugates of said peptidomimetics and a moiety of a payload selected from fluorescent probes, photosensitizers, chelating agents, or cytotoxic agents; and pharmaceutical compositions comprising these conjugates. The conjugates of the invention are useful both for diagnostic purposes and treatment of various diseases, disorders and conditions. More specifically, conjugates comprising fluorescent probes can be used for diagnostic purposes, e.g., visualization of organs and tissues, and diagnosis of tumors; conjugates comprising photosensitizers can be used for photodynamic therapy of both tumors and nonneoplastic tissues; conjugates comprising chelating agents can be used in radio imaging or radiotherapy; and conjugates comprising cytotoxic agents can be used for in targeted chemotherapy.

13 Claims, 6 Drawing Sheets

(56) References Cited

OTHER PUBLICATIONS

Locardi, Elsa et al., "Conformations and Pharmacophores of Cyclic RGD Containing Peptides which Selectively Bind Integrin AlphavBeta3", Journal of Peptide Science, vol. 5, pp. 491-506, (1999).

Pasqualini, Renata et al., "Aminopeptidase N is a Receptor for Tumor-homing Peptides and a Target for Inhibiting Angiogenesis", Cancer Research, vol. 60, pp. 722-727, (2000).

Pasqualini, Renata et al., "Alphav Integrins as receptors for tumor targeting by circulating ligands", Nature Biotechnology, vol. 15, pp. 542-546, (1997).

Pasqualini, Renata et al; "Organ targeting In vivo using phage display peptide libraries", Nature, vol. 380, pp. 364-366,(1996).

Raboisson, Pierre et al., "Novel potent and selective $\alpha v\beta 3/\alpha v\beta 5$ integrin dual antagonists with reduced binding affinity for human serum albumin", European Journal of Medicinal Chemistry, vol. 41, pp. 847-861, (2006).

Romanov, Victor I. et al., "RGD-Recognizing Integrins Mediate Interactions of Human Prostate Carcinoma Cells With Endothelial Cells In Vitro", The Prostate, vol. 39, pp. 108-118, (1999).

Ruoslahti, Erkki, "RGD and other recognition sequences for integrins", Annual Review of Cell and Developmental Biology, vol. 12, pp. 697-715, (1996).

Ruoslahti, Erkki et al., "An address system in the vasculature of normal tissues and tumors", Annual Review of Immunology, vol. 18, pp. 813-827, (2000).

Ruoslahti, Erkki, "Targeting tumor vasculature with homing peptides from phage display", seminars in Cancer Biology, vol. 10, pp. 435-442, (2000).

Saiki, I. et al., "Antimetastatic effects of synthetic polypeptides containing repeated structures of the cell adhesive Arg-Gly-Asp (RGD) and Tyr-Ile-Gly-Ser-Arg (YIGSR) sequences", British Journal of Cancer, vol. 60, pp. 722-728, (1989).

Su, Zi-Fen et al., "In Vitro and in Vivo Evaluation of a Technetium-99m-Labeled Cyclic RGD Peptide as a Specific Marker of $\alpha v\beta 3$ Integrin for Tumor Imaging", Bioconjugate Chemistry, vol. 13, pp. 561-570, (2002).

Van Hagen, P.M. et al., "Evaluation of a Radiolabelled Cyclic DTPA-RGD Analogue for Tumour Imaging and Radionuclide Therapy", International Journal of Cancer, vol. 90, pp. 186-198, (2000).

Zitzmann, Sabine et al., "Arginine-Glycine-Aspartic Acid (RGD)-Peptide Binds to Both Tumor and Tumor-Endothelial Cells in Vivo", Cancer Research, vol. 62, pp. 5139-5143, (2002).

Red fluorescent protein (RFP)          Conjugate 1

Red fluorescent protein (RFP)          Conjugate 4

Red fluorescent protein (RFP)          Conjugate 41

RGD-CONTAINING PEPTIDOMIMETICS AND USES THEREOF

TECHNICAL FIELD

The present invention relates to novel arginine-glycine-aspartic acid (RGD)-containing cyclic peptidomimetics and uses thereof, e.g., in cancer diagnostics and treatment.

Abbreviations: AcOH, acetic acid; Alloc, allyloxy carbonyl; Bpheide, Bacteriopheophorbide; BTA, (BPheide taurine amide), $3^1$-oxo-15-methoxy carbonylmethyl-rhodobacterioclorin $13^1$-(2-sulfoethyl)amide; BTC, Bis (trichloromethyl) carbonate; Dab, diaminobutyric acid; Dap, diaminopropionic acid; DCM, dichloromethane; Dde, 1-(4,4-dimethyl-2,6-dioxocyclohexylidene) ethyl; DIC, diisopropylcarbodiimide; DIEA, diisopropylethylamine; DMBA, dimethylbarbituric acid; DMF, N,N-dimethyl formamide; DMSO, dimethyl sulfoxide; DOTA, 1,4,7,10-tetraazacyclododecane-1,4,7,10-tetraacetic acid; DTPA, diethylenetriaminepentaacetic acid; $Et_2O$, diethyl ether; FITC, fluoresceinisothiocyanate; Fmoc, fluorenylmethoxycarbonyl; GABA, γ-aminobutyric acid; HATU, 0-(7-azabenzotriazol-1-yel)-1,1,3,3-tetramethyluronium hexafluorophosphate; HOAt, 1-hydroxy-7-azabenzotriazole; HOBt, N-hydroxybenzotriazole; Lys, lysine; MeOH, methanol; Nal, naphthylalanine; Orn, ornithine; Pbf, 2,2,4,6,7-pentamethyl-dihydrobenzofurane-5-sulfonyl; PyBOP, benzotriazole-1-yl-oxy-tris-pyrrolidino-phosphonium hexafluorophosphate; RP-HPLC, reverse phase high performance liquid chromatography; RT, room temperature; TFA, trifluoroacetic acid; TFE, trifluoroethanol; TIS, triisopropylsilane.

BACKGROUND ART

The arginine-glycine-aspartic acid (Arg-Gly-Asp; RGD) motif of extracellular matrix (ECM) components such as fibronectin (Pierschbacher and Ruoslahti, 1984) and vitronectin binds to integrins (Ruoslahti and Pierschbacher, 1987; D'Souza S E et al., 1991; Joshi et al, 1993; Koivunen et al., 1994). Integrin-mediated adhesion leads to intracellular signaling events that regulate cell survival, proliferation and migration. About 25 integrins are known, and at least eight of them bind the RGD motif as the primary recognition sequence in their ligands.

Data obtained by phage display methods (Pasqualini and Ruoslahti, 1996) screening for RGD-containing peptides have shown their selective binding to endothelial lining of tumor blood vessels (Ruoslahti, 1996; Pasqualini et al., 1997).

Because the expression of integrins is reported to be high on activated, but more restricted on quiescent, endothelial cells (ECs), small synthetic RGD-containing peptides have been proposed as antagonists impairing the growth of vascular endothelial and tumor cells. RGD peptides also retard signal transmission, affect cell migration and induce tumor cell regression or apoptosis (Su et al., 2002). RGD-analogues are used in tumor imaging (Haubner et al., 2001), anti-angiogenesis approaches (Kawaguchi et al., 2001; Pasqualini et al., 2000), and in tumor targeting of radionucleotides (van Hagen et al., 2000) and chemotherapeutic drugs (Arap et al., 1998; Zitzmann et al., 2002).

Integrins are also expressed on cancer cells and play an important role in the invasion, metastasis, proliferation and apoptosis of cancer cells. Metastatic invasion of tumor cells into preferred organs may represent cell-homing phenomena that depend on the adhesive interaction between the tumor cells and organ-specific endothelial markers (Ruoslahti and Rajotte, 2000). By binding to integrin of either endothelial or tumor cells, RGD peptides are capable of modulating in vivo cell traffic by inhibition of tumor cell-ECM and tumor cell-EC attachments, which are obligatory for metastatic processes. Several studies have indicated that RGD-containing compounds can interfere with tumor cell metastatic processes in vitro (Goligorsky et al., 1998; Romanov and Goligorsky 1999) and in vivo (Saiki et al., 1989; Hardan et al., 1993).

Peptides that are specific for individual integrins are of considerable interest and of possible medical significance. The $\alpha_v\beta_3$ integrin was the first integrin shown to be associated with tumor angiogenesis. RGD peptides that specifically block the $\alpha_v\beta_3$ integrin show promise as inhibitors of tumor and retinal angiogenesis, of osteoporosis and in targeting drugs to tumor vasculature (Assa-Munt et al., 2001). Coupling of the anticancer drug doxorubicin or a pro-apoptotic peptide to an $\alpha_v\beta_3$ integrin-binding RGD peptide yields compounds that are more active and less toxic than unmodified drugs when tested against xenograft tumors in mice (Ruoslahti, 2000; Arap et al., 1998; Arap et al., 2002; Ellerby et al., 1999). Consequently, a great amount of work was invested in designing and producing integrin-binding peptides and peptidomimetics (Haubner et al., 1996; Locardi et al., 1999; Lark et al., 1999; Raboisson et al., 2006; Belvisi et al., 2005; Dijkgraaf et al., 2006; Banfi et al., 2007; U.S. Pat. No. 5,849, 692).

U.S. Pat. No. 6,576,239, EP 0927045 and WO 98/010795 disclose a conjugate comprising a tumor horning peptide comprising the amino acid sequence RGD or NGR, said peptide linked to a therapeutic or diagnostic moiety, provided said moiety is not a phage particle. The therapeutic moiety may be a cytotoxic agent or a cancer chemotherapeutic agent such as doxorubicin. The conjugate selectively homes to angiogenic vasculature upon in vivo administration. The tumor homing peptide may be a linear or cyclic peptide of up to 20 or 30 amino acids or of 50-100 amino acids in length. One preferred peptide is the cyclic nonapeptide CDCRGD-CFC or H-Cys*-Asp-Cys*-Arg-Gly-Asp-Cys*-Phe-Cys*-NH$_2$.

WO 2008/023378 discloses a conjugate of an RGD-containing peptide or an RGD peptidomimetic and a photosensitizer selected from a porphyrin, a chlorophyll or a bacteriochlorophyll.

SUMMARY OF INVENTION

In one aspect, the present invention relates to an RGD-containing cyclic peptidomimetic of the general formula I:

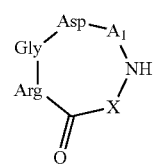

wherein
the arginine residue is linked via its α-amino group to the backbone C=O;
X is —NH—, —NH—R—, —O—R—, —S— or —S—R—, R is a hydrocarbylene radical derived from a $C_1$-$C_6$ alkane, a $C_2$-$C_6$ alkene, a $C_2$-$C_6$ alkyne, a $C_3$-$C_{10}$ cycloalkane, a $C_3$-$C_{10}$ cycloalkene, a $C_6$-$C_{14}$ mono- or polycyclic aromatic hydrocarbon, or a $C_6$-$C_{14}$ mono- or polycyclic aromatic hydrocarbon substituted by one or two $C_1$-$C_2$ alkyl, $C_2$ alkenyl or $C_2$ alkynyl, or R together with the nitrogen atom to which it is attached form a 5- or 6-membered saturated or unsaturated heterocyclic ring optionally containing 1-2 further heteroatoms selected from oxygen, nitrogen or sulfur; and $A_1$ is a natural or non-natural amino acid residue bearing either an amino or carboxyl group on its side chain, linked via its α- or side chain carboxyl group to the backbone NH and via its α- or side chain amino group to the α-carboxyl group of the aspartic acid residue, or of the general formula II:

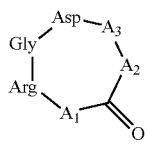

II wherein $A_1$ is a natural or non-natural amino acid residue bearing either an amino or carboxyl group on its side chain, linked via its α- or side chain carboxyl group to the α-amino group of the arginine residue and via its α- or side chain amino group to the backbone C=O;

$A_2$ is a natural or non-natural amino acid residue linked via its α-amino group to the backbone C=O and via its α-carboxyl group to the α- or side chain amino group of $A_3$; and $A_3$ is a natural or non-natural amino acid residue bearing an amino group on its side chain and amidated at its C-terminus, linked via one of its α- or side chain amino group to the carboxyl group of $A_2$ and via another of its α- or side chain amino group to the α-carboxyl group of the aspartic acid residue.

In another aspect, the present invention relates to a conjugate of the RGD-containing cyclic peptidomimetic defined above and a moiety of a payload selected from a fluorescent probe, a photosensitizer, a chelating agent or a cytotoxic agent, linked to the amino acid residue $A_1$ in the peptidomimetic, provided that when $A_1$ has a side chain amino group, said payload moiety is linked to either the α- or side chain amino group of $A_1$, optionally via a spacer, and when $A_1$ is a dicarboxylic amino acid residue, said payload moiety is linked to either the α- or side chain carboxyl group of $A_1$, optionally via a spacer.

In a further aspect, the present invention provides a pharmaceutical composition comprising a conjugate of an RGD-containing cyclic peptidomimetic and a payload moiety as defined above, or a pharmaceutically acceptable salt thereof, and a pharmaceutically acceptable carrier.

The pharmaceutical compositions of the present invention may be used for various purposes, e.g., (i) for diagnostic purposes, in particular, for visualization of organs and tissues and for diagnosis of tumors, when the payload is a fluorescent probe; (ii) for photodynamic therapy (PDT), in particular, for PDT of tumors or nonneoplastic tissues, when the payload is a photosensitizer; (iii) for radio imaging or radiotherapy, when the payload is a chelating agent; and (iv) for targeted chemotherapy, when the payload is a cytotoxic agent.

In still another aspect, the present invention thus relates to use of a conjugate of an RGD-containing cyclic peptidomimetic and a payload moiety as defined above, or a pharmaceutically acceptable salt thereof, for the preparation of a pharmaceutical composition for diagnostic purposes, photodynamic therapy (PDT), radio imaging or radiotherapy, or targeted chemotherapy.

In still a further aspect, the present invention relates to a conjugate of an RGD-containing cyclic peptidomimetic and a payload moiety as defined above, or a pharmaceutically acceptable salt thereof for diagnostic purposes, photodynamic therapy (PDT), radio imaging or radiotherapy, or targeted chemotherapy.

MODES FOR CARRYING OUT THE INVENTION

Figure 1A:
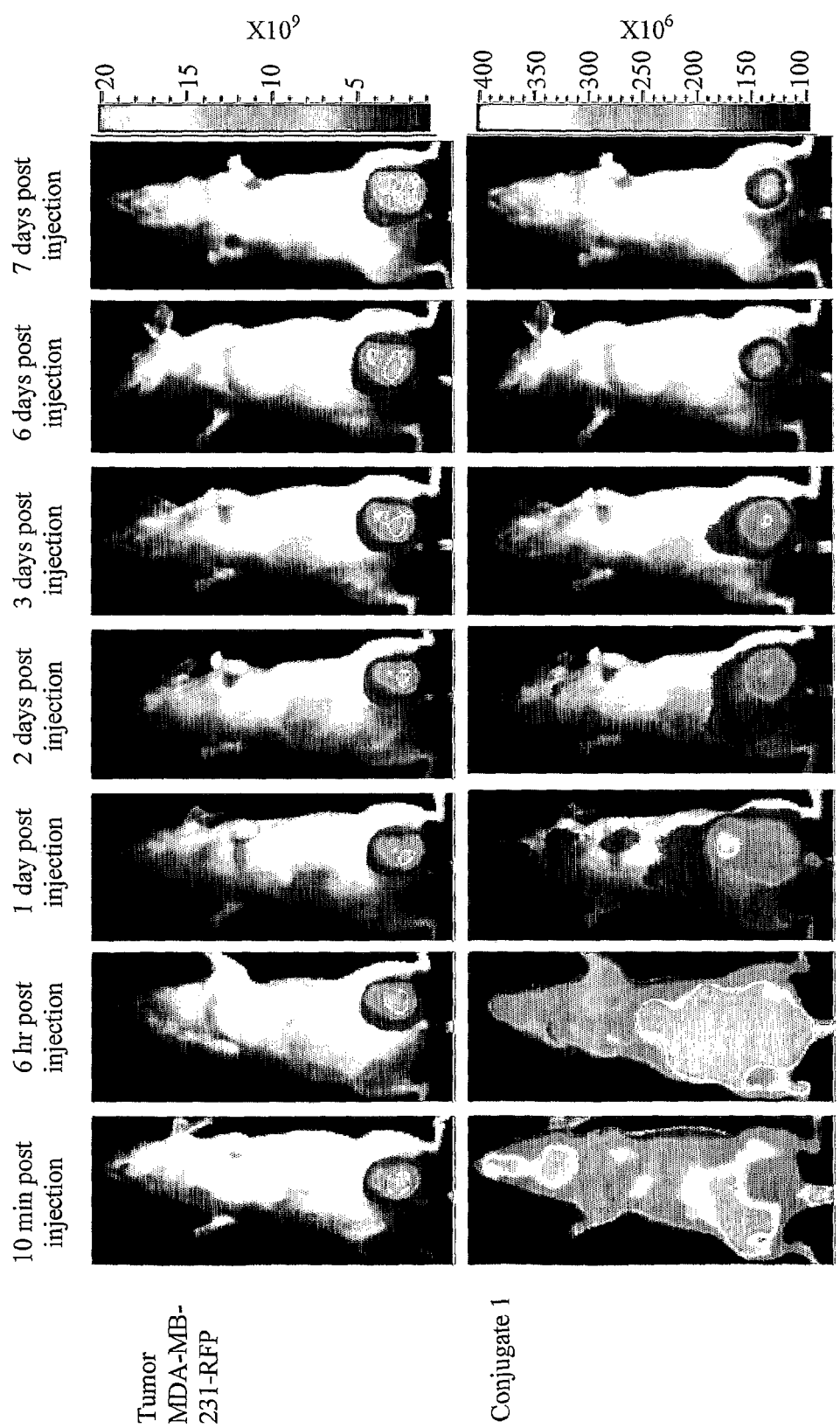
FIGS. 1A-1C show the accumulation patterns of conjugates 1, 4 and 41 (1A, 1B and 1C, respectively) in orthotopic human breast MDA-MB-23'-RFP primary large tumor in the mammary pad of CD-1 nude mice. Mice were treated as described in Materials and Methods, and the fluorescence of both the tumor cells and the conjugate were monitored from day 1 to 7 using the Xenograph IVIS® system (color scale in units of photon/sec/cm²/steradian). Upper panel shows the fluorescent signals generated by the tumor (red fluorescence imaging) and lower panel shows the fluorescent signal generated by the conjugate (near-infrared fluorescence imaging). Matching of the signals generated by the tumor and by the conjugate suggests accumulation of the conjugate in the tumors.

In one aspect, the present invention provides novel arginine-glycine-aspartic acid (Arg-Gly-Asp; RGD)-containing cyclic peptidomimetics, which are $α_vβ_3$ and $α_vβ_5$ integrin ligands, as defined above.

The terms "RGD-containing cyclic peptidomimetic", "cyclic peptidomimetic" and "$\alpha_v\beta_3$ and $\alpha_v\beta_5$ integrin ligand" used herein interchangeably refer to a cyclic non-peptidic compound containing the RGD sequence, also referred to as the RGD motif, which mimics peptides having the RGD motif. The cyclic peptidomimetic of the present invention may be any cyclic compound having either the general formula I or the general formula II, as defined above.

As shown in detail in Scheme 1 hereinafter, the RGD-containing cyclic peptidomimetic of the general formula I is a cyclic compound containing the RGD motif, in which a residue of either a dicarboxylic amino acid or an amino acid having a side chain amino group ($A_1$) is linked by amide bonds to the α-carboxyl group of the aspartic acid residue in the RGD motif on one side and to a backbone NH on the other side, and said backbone NH is linked to the α-amino group of the arginine residue in the RGD motif via various possible bridging units. As further shown, the RGD-containing cyclic peptidomimetic of the general formula II is a cyclic compound containing the RGD motif, in which a residue of either a dicarboxylic amino acid or an amino acid having a side chain amino group ($A_1$) is linked by amide bond to the α-amino group of the arginine residue in the RGD motif on one side and via an amino group thereof to a backbone C=O on the other side, wherein the backbone C=O is linked to the α-amino group of another amino acid residue ($A_2$), which is linked by amide bond to a residue of a further amino acid having a side chain amino group and amidated at its C-terminus ($A_3$) that is linked by amide bond to the α-carboxyl group of the aspartic acid residue in the RGD motif.

The term "hydrocarbylene" refers to a divalent radical containing only carbon and hydrogen atoms that may be saturated or unsaturated, linear or branched, cyclic or acyclic, or aromatic, which may be derived from a $C_1$-$C_6$ alkane, a $C_2$-$C_6$ alkene, a $C_2$-$C_6$ alkyne, a $C_3$-$C_{10}$ cycloalkane, a $C_3$-$C_{10}$ cycloalkene, a $C_6$-$C_{14}$ mono- or polycyclic aromatic hydrocarbon, or a $C_6$-$C_{14}$ mono- or polycyclic aromatic hydrocarbon substituted by one or two $C_1$-$C_2$ alkyl, $C_2$ alkenyl or $C_2$ alkynyl.

Scheme 1: Detailed structures of the cyclic peptidomimetic of the general formula I (left side) and II (right side)

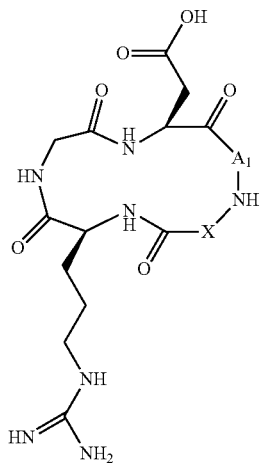

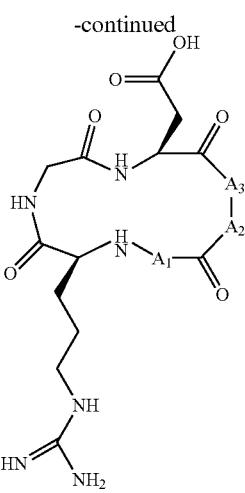

The term "$C_1$-$C_6$ alkane" typically means a straight or branched hydrocarbon having 1-6 carbon atoms and includes, for example, methane, ethane, n-propane, isopropane, n-butane, isobutane, n-pentane, 2,2-dimethylpropane, n-hexane, and the like. Preferred are $C_1$-$C_4$ alkanes, more preferably ethane. The terms "$C_2$-$C_6$ alkene" and "$C_2$-$C_6$ alkyne" typically mean straight and branched hydrocarbon having 2-6 carbon atoms and one double or triple bond, respectively, and include ethene, 3-butene, 2-ethenylbutene, and the like, and propyne, 2-butyne, 3-pentyne, and the like. The term "$C_3$-$C_{10}$ cycloalkane" means a cyclic or bicyclic hydrocarbon such as cyclopropane, cyclobutane, cyclopentane, cyclohexane, and the like, and the term "$C_6$-$C_{14}$ mono- or polycyclic aromatic hydrocarbon" denotes a carbocyclic aromatic molecule such as benzene, naphthalene and anthracene.

In the group NHR, R is a hydrocarbylene as defined above, or R together with the nitrogen atom to which it is attached form a saturated, preferably a 5- or 6-membered, heterocyclic ring, optionally containing 1 or 2 further heteroatoms selected from oxygen, nitrogen or sulfur. Such rings may be substituted, e.g., with one or two $C_1$-$C_6$ alkyl groups, or with one alkyl or hydroxyalkyl group at a second nitrogen atom of the ring, e.g., in a piperazine ring.

The term "amino acid" refers to both natural and non-natural amino acids in their L and D stereoisomers, and includes, inter alia, amino acids having a side chain amino group as well as dicarboxylic amino acids. Non-limiting examples of amino acids having a side chain amino include lysine (Lys), diaminopropionic acid (Dap), diaminobutyric acid (Dab) and ornithine (Orn); and examples of dicarboxylic acids, without limiting, include glutamic acid (Glu), aspartic acid (Asp) and aminoadipic acid.

In one embodiment, the RGD-containing cyclic peptidomimetic of the present invention is a cyclic compound of the general formula I, wherein X is —NH— or —NH—R—, i.e., an urea moiety is formed with the α-amino group of the arginine residue, and R is a hydrocarbylene derived from a linear $C_2$-$C_6$ alkane, a $C_2$-$C_6$ alkene or a $C_2$-$C_6$ alkyne, preferably from a $C_2$-$C_4$ alkane, a $C_2$-$C_4$ alkene or a $C_2$-$C_4$ alkyne, more preferably from ethane.

In another embodiment, the RGD-containing cyclic peptidomimetic of the present invention is a cyclic compound of the general formula I, wherein X is —NH—R— and R is a hydrocarbylene derived from a $C_6$-$C_{14}$ mono- or polycyclic aromatic hydrocarbon substituted by two $C_1$-$C_2$ alkyl, preferably 1,3-dimethylbenzene-1,3-diyl, i.e., m-xylene linked via the methyl groups.

In a further embodiment, the RGD-containing cyclic peptidomimetic of the present invention is a cyclic compound of the general formula I, wherein X is —NH—R— and R together with the nitrogen atom to which it is attached form a 5- or 6-membered saturated or unsaturated heterocyclic ring, preferably piperidine-1,4-diyl, i.e., piperidine linked via positions 1 and 4.

In still another embodiment, the RGD-containing cyclic peptidomimetic of the present invention is a cyclic compound of the general formula I, wherein X is —O—R—, i.e., a carbamate moiety is formed with the α-amino group of the arginine residue, and R is a hydrocarbylene derived from a linear $C_2$-$C_6$ alkane, a $C_2$-$C_6$ alkene or a $C_2$-$C_6$ alkyne, preferably from a $C_2$-$C_4$ alkane, a $C_2$-$C_4$ alkene or a $C_2$-$C_4$ alkyne, more preferably from ethane.

In yet another embodiment, the RGD-containing cyclic peptidomimetic of the present invention is a cyclic compound of the general formula I, wherein X is —S— or —S—R—, i.e., a carbamothio moiety is formed with the α-amino group of the arginine residue, and R is a hydrocarbylene derived from a linear $C_2$-$C_6$ alkane, a $C_2$-$C_6$ alkene or a $C_2$-$C_6$ alkyne, preferably from a $C_2$-$C_4$ alkane, a $C_2$-$C_4$ alkene or a $C_2$-$C_4$ alkyne, more preferably from ethane.

In still a further embodiment, the RGD-containing cyclic peptidomimetic of the present invention is a cyclic compound of the general formula II, wherein $A_1$ is a residue of an amino acid having a side chain amino group such as Lys, Dap, Dab and Orn, preferably Lys, or a residue of a dicarboxylic amino acid such as Glu, Asp and aminoadipic acid.

In yet a further embodiment, the RGD-containing cyclic peptidomimetic of the present invention is a cyclic compound of the general formula II, wherein $A_2$ is a residue of an amino acid such as phenylalanine (Phe), D-phenylalanine (D-Phe), valine (Val), Gly and Asp.

In yet another embodiment, the RGD-containing cyclic peptidomimetic of the present invention is a cyclic compound of the general formula II, wherein $A_3$ is a residue of an amino acid having a side chain amino group such as Lys, Dap, Dab and Orn, amidated at its C-terminus.

The RGD-containing cyclic peptidomimetics of the present invention may be prepared by any method known in the art, e.g., as described in Materials and Methods hereinafter.

In one preferred embodiment, the RGD-containing cyclic peptidomimetic of the present invention is a cyclic compound of the general formula I, wherein X is —NH— and $A_1$ is Dap.

In other preferred embodiments, the RGD-containing cyclic peptidomimetic of the present invention is a cyclic compound of the general formula I, wherein X is —NH—R—, R is a hydrocarbylene derived from ethane and $A_1$ is Dap, Dab, Orn or Lys.

In further preferred embodiments, the RGD-containing cyclic peptidomimetic of the present invention is a cyclic compound of the general formula I, wherein X is —NH—R—, R is a hydrocarbylene derived from propane, n-butane or n-hexane, and $A_1$ is Orn.

In yet other preferred embodiments, the RGD-containing cyclic peptidomimetic of the present invention is a cyclic compound of the general formula I, wherein X is —O—R—, R is a hydrocarbylene derived from ethane and $A_1$ is Dap or Lys.

In still further preferred embodiments, the RGD-containing cyclic peptidomimetic of the present invention is a cyclic compound of the general formula II, wherein $A_1$ is Lys, $A_2$ is Phe, Val, D-Phe or Asp, and $A_3$ is Dap amidated at its C-terminus.

In yet further preferred embodiments, the RGD-containing cyclic peptidomimetic of the present invention is a cyclic compound of the general formula II, wherein $A_1$ is Lys, $A_2$ is Phe and $A_3$ is Dab, Orn or Lys, amidated at its C-terminus.

The $\alpha_v\beta_3$ and $\alpha_v\beta_5$ integrin ligands of the present invention accumulate in tumors expressing $\alpha_v\beta_3$ and $\alpha_v\beta_5$ such as ovarian carcinoma, colon, breast and prostate cancer, and therefore can be used in both diagnostic and therapeutic methods by conjugation to various "payload" moieties.

In another aspect, the present invention thus relates to a conjugate of an RGD-containing cyclic peptidomimetic defined above, i.e., a cyclic peptidomimetic of the general formula I or II, and a moiety of a payload selected from a fluorescent probe, a photosensitizer, a chelating agent or a cytotoxic agent, linked to the amino acid residue $A_1$ in the peptidomimetic, provided that when $A_1$ has a side chain amino group, said payload moiety is linked to either the α- or side chain amino group of $A_1$, optionally via a spacer, and when $A_1$ is a dicarboxylic amino acid residue, said payload moiety is linked to either the α- or side chain carboxyl group of $A_1$, optionally via a spacer.

In one embodiment, the payload moiety of the conjugate is linked directly to the amino acid residue $A_1$ of the cyclic peptidomimetic.

In another embodiment, the payload moiety is linked to the amino acid residue $A_1$ of the cyclic peptidomimetic via a spacer.

The spacer linking the payload moiety to the amino acid residue $A_1$ in the cyclic peptidomimetic of the present invention may be selected from a moiety of a natural or non-natural amino acid, a moiety of a small peptide having not more than 8 amino acids, a diamine residue, a $C_1$-$C_{25}$ hydrocarbylene, or a soluble polymer.

In one embodiment, the spacer is a moiety of a natural or non-natural amino acid such as, without being limited to, Gly, β-alanine (β-Ala), Phe, D-Phe, 1-naphthylalanine (1-Nal), D-1-naphthylalanine (D-1-Nal), γ-aminobutiric acid GABA) and 3-(aminomethyl)benzoic acid. In cases $A_1$ of the cyclic peptidomimetic is a residue of an amino acid bearing a side chain amino group, these spacers are linked via their α-carboxyl group to the α- or side chain amino group of $A_1$ and via their α-amino group to a carboxyl group of the payload. Alternatively, in cases $A_1$ is a residue of a dicarboxylic amino acid, the spacers are linked via their α-amino group to the α- or side chain carboxyl group of $A_1$ and via their α-carboxyl group to an amino group of the payload.

In another embodiment, the spacer is a moiety of a small peptide having not more than eight amino acids. In cases $A_1$ of the cyclic peptidomimetic is a residue of an amino acid bearing a side chain amino group, these spacers are linked via their C-terminal carboxyl group to the α- or side chain amino group of $A_1$ and via their N-terminal amino group to a carboxyl group of the payload. Alternatively, in cases $A_1$ is a residue of a dicarboxylic amino acid, the spacers are linked via their N-terminal amino group to the α- or side chain carboxyl group of $A_1$ and via their C-terminal carboxyl group to an amino group of the payload.

In a further embodiment, the spacer is a diamine residue of the general formula —HN—R'—NH—, wherein R' is absent or is a divalent radical containing only carbon and hydrogen atoms that may be saturated or unsaturated, linear or branched, cyclic or acyclic, or aromatic, which may be derived from a $C_1$-$C_{12}$ alkane, a $C_2$-$C_{12}$ alkene, a $C_2$-$C_{12}$ alkyne, a $C_3$-$C_{10}$ cycloalkane, a $C_3$-$C_{10}$ cycloalkene, a $C_6$-$C_{14}$ mono- or polycyclic aromatic hydrocarbon, or a $C_6$-$C_{14}$ mono- or polycyclic aromatic hydrocarbon substituted by one or two $C_1$-$C_2$ alkyl, $C_2$ alkenyl or $C_2$ alkynyl. Non-limiting examples of diamines from which such residues may be derived include hydrazine, 1,2-ethylenediamine, 1,3-propylenediamine, 1,4-diaminobutane, 1,5-diaminopentane, 1,6-diaminohexane, 1,7-diaminoheptane, 1,8-diaminooctane, 1,9-diaminononane, 1,10-diaminodecane, 1,11-diaminoundecane, 1,12-diaminododecane, p-phenylenediamine, cyclopentane 1,3-diamine, cyclohexane 1,4-diamine, cycloheptane 1,4-diamine, cyclooctane 1,5-diamine, naphthalene-2,6-diamine and 9H-fluorene-3-6-diamine.

In still another embodiment, the spacer is a $C_1$-$C_{25}$ hydrocarbylene, preferably a $C_1$-$C_{10}$ alkylene or phenylene, substituted by two end functional groups through which the spacer is bound to either the α- or side chain amino or carboxyl of the amino acid $A_1$ of the cyclic peptidomimetic on one hand, and to the payload moiety on the other hand. Such end functional groups may be selected from OH, COOH, $SO_3H$, COSH or $NH_2$, thus forming an ether, ester, amide, urea, thioamide or sulfonamide group.

In yet another embodiment, the spacer is a soluble polymer such as, without being limited to, linear or branched polyethylene glycol (PEG) or copolymers thereof, polylactide (PLA) or copolymers thereof, polyesters having suitable functional groups based on PLA, polyglycolide (PGA), polycaprolactone (PCL), or their copolymers, or polyamides based on polymethacrylamide or their copolymers, said polymers having suitable functional groups for linking to the amino acid residue $A_1$ of the cyclic peptidomimetic and to the payload moiety, said functional groups being, e.g., hydroxy, amino, carboxyl, mercapto, sulfonic acid group, and the like.

Example 1 hereinafter describes the synthesis of various conjugates, herein identified by the Arabic numbers 1-36 in bold, in which different $α_vβ_3$ and $α_vβ_5$ integrin ligands of the general formula I are linked either directly or via a spacer to a fluorescent probe, in particular, BTA, FITC or dansyl; a bacteriochlorophyll derivative, in particular, Pd-BTA; or a chelating agent, in particular, DTPA or DOTA. The list of conjugates prepared, as well as their structural characteristics, is summarized in Table 1. Example 2 describes the synthesis of various conjugates, herein identified by the Arabic numbers 41-48 in bold, in which different $α_vβ_3$ and $α_vβ_5$ integrin ligands of the general formula II are linked directly to a moiety of the fluorescent probe BTA as a model payload. The list of conjugates prepared, as well as their structural characteristics, is summarized in Table 2. The chemical structures of the various payload moieties used, when linked to a cyclic peptidomimetic, are depicted in Scheme 2.

Conjugates 1-36 were tested for binding to MLS human ovarian carcinoma cells, using both in vitro integrin binding assay and in vivo ovarian carcinoma model. Some of these conjugates were tested for binding to HT29 human colon carcinoma cell as well, both in vivo and in vitro, and conjugates 1 and 4 were further tested for binding to LNCaP prostate cancer cells, both in vitro and in vivo. Conjugates 41-48 were tested for binding to MLS human ovarian carcinoma cells, using in vitro integrin binding assay, and the active conjugates were tested using an in vivo ovarian carcinoma model as well. Conjugates 41 and 42 were tested for binding to HT29 human colon carcinoma cells, both in vivo and in vitro, and conjugate 41 was further tested for binding to LNCaP prostate cancer cells, both in vitro and in vivo.

When screening the biological activity of different conjugates based on RGD-containing cyclic peptidomimetics of the general formula I, it has been found that certain structural characteristics of the cyclic peptidomimetic, i.e., the ring size of the cyclic compound and the size and structure of the diamine residue present in some of the cyclic compounds, as well as the spacer linking the cyclic compound and the payload moiety, may affect the biological activity of the conjugate as described hereinbelow.

Example 3 hereinafter shows the biological activity of various fluorescent probe-conjugates comprising cyclic peptidomimetics of the general formula I with different ring sizes. The ring size of the cyclic peptidomimetic was altered by changing two structural parameters of the cyclic compound, in particular, (i) the amino acid residue linked via its α- or side-chain carboxyl group to the backbone NH and via its α- or side-chain amino group to the α-carboxyl group of the aspartic acid residue, i.e., $A_1$ in the general formula I; and (ii) the radical bridging the backbone carbonyl and the backbone NH, i.e., radical X in the general formula I. The specific amino acid residues $A_1$ used were residues of Dap, Dab, Orn or Lys, having one to four methylene units in the side chain, respectively; and the different radicals X used were —NH—, —$NH(CH_2)_{2-4}$— and —$NH(CH_2)_6$—, which, together with the backbone NH, form a moiety of either hydrazine or a certain alkyldiamine. As particularly shown, the biological activity of the conjugates tested increased with increasing the ring size of the cyclic peptidomimetic from 16 atoms to 19-20 atoms; however, it decreased with further increasing the ring size. These results indicate that whereas the urea bond bridging the α-amino group of the arginine residue and radical X makes the cyclic compound more rigid, a larger ring having up to 19-20 atoms is more flexible to adopt the desired conformation for binding to the integrin. On the other hand, in cases wherein the ring size of the cyclic peptidomimetic is higher than 20 atoms, the cyclic compound probably cannot adopt the desired conformation for binding to the integrin.

Example 4 shows the biological activity of various BTA-conjugates comprising cyclic peptidomimetics of the general formula I having different diamine residues linked by amide bonds to either the α- or side-chain carboxyl group of the amino acid residue $A_1$ and, via the backbone C=O, to the α-amino group of the arginine residue. The specific conjugates tested were such in which the amino acid residue $A_1$ is Orn, the BTA moiety is directly linked to the N-terminal of the peptidomimetic ring, and the radical designated X is a radical of the formula —$NH(CH_2)_{2-4}$—, 1,3-dimethylbenzene-1,3-diyl or piperidine-1,4-diyl. As particularly shown, the biological activity of the conjugates in which an alkyldiamine residue is bridging $A_1$ and the backbone C=O decreased with increasing the length of the alkyl chain. Furthermore, in cases where the radical designated X was derived from m-xylene or piperidine, no biological activity was measured, indicating that the peptidomimetic rings in such conjugates are rigid and adopt a conformation undesirable for the interaction with the integrin.

Example 5 shows the biological activity of various fluorescent probe-conjugates comprising cyclic peptidomimetics of the general formula I having different spacers linking the N-terminal of the cyclic peptidomimetic and the fluorescent probe moiety. The specific spacers used were moieties of different natural or non-natural amino acids, in particular, Gly, β-Ala, Phe, D-Phe, 1-Nal, D-1-Nal, GABA and 3-(aminomethyl)benzoic acid, or residues of different diamines, in particular, 1,2-ethylenediamine and 1,4-diaminobutane. As shown, BTA conjugates in which the fluorescent probe moiety is directly linked to the cyclic peptidomimetic showed high biological activity, probably because the BTA moiety does not interfere with the binding of the cyclic compound to the integrin. Contrary to that, conjugates in which Gly or β-Ala moieties were used as spacers, having an increased distance between the cyclic peptidomimetic and the BTA moiety, showed lower activity, probably due to the bulkiness of the BTA moiety. Interestingly, when the distance between the cyclic peptidomimetic and the BTA moiety was further increased using a GABA moiety as a spacer, the biological activity of the conjugate was higher than that of the conjugates in which Gly or β-Ala moieties were used as spacers, possibly indicating that GABA is long enough for giving more freedom to the cyclic peptidomimetic to bind to the integrin; however, not too long to cause folding of the BTA moiety over the peptidomimetic ring. In cases FITC and dansyl, which are smaller than BTA, were used, the distance between the fluorescent probe moiety and the N-terminal of the cyclic peptidomimetic had no influence on the biological activity of the conjugate. As further shown, BTA-conjugates in which Phe, 1-Nal, D-Phe or D-1-Nal moieties were used as spacers were more active than the corresponding conjugate in which a Gly moiety was used, probably because of the aromatic side chain of phenylalanine or naphthylalanine, which provides interaction with a hydrophobic pocket of the integrin. It is worth noting that the biological activity of the conjugate in which a D-Phe moiety was used as a spacer was higher than that of the conjugates in which Phe or 1-Nal moieties were used, indicating that the D configuration may fit the hydrophobic pocket of the integrin better than the L configuration. D-1-Nal is less reactive than D-Phe, indicating that the phenyl ring fit the hydrophobic pocket better than the naphthyl. It should be noted that conjugates 32 and 33, in which residues of 1,2-ethylenediamine or 1,4-diaminobutane, respectively, were used as spacers and an urea bond is formed between the cyclic peptidomimetic and the spacer, had biological activity similar to that of conjugates 10 and 11, indicating that the urea bond has nearly the same activity as the amide bond and it does not influence the conformation of the peptidomimetic. The strong biological activity of conjugate 33, compared with that of conjugate 32, may be due to the distance of four methylene units between the peptidomimetic ring and the payload moiety, which gives more freedom to the peptidomimetic ring to interact with the binding site of the integrin.

On the other hand, Example 6 shows that BTA-conjugates comprising cyclic peptidomimetics of the general formula I in which an urea moiety is formed with the α-amino of the arginine residue had a biological activity similar to that of the corresponding conjugates in which a carbamate moiety is formed, indicating that the nature of the moiety formed with the α-amino of the arginine residue has no effect on the biological activity of the conjugate.

Example 7 describes the synthesis of four unmetalated bacteriochlorophyll derivative-conjugates herein identified by the Arabic numbers 37-40, consisting of different $\alpha_v\beta_3$ and $\alpha_v\beta_5$ integrin ligands of the general formula I linked directly to a BTA derivative moiety in which the taurine was replaced by a different nucleophile. As shown, the biological activity of these conjugates, measured using an in vitro integrin binding assay, was similar, indicating that in these cases, the amino group has no effect on the biological activity and its behavior is nearly the same as that of the sulphonate in taurine.

When screening the biological activity of different conjugates based on RGD-containing cyclic peptidomimetics of the general formula II, it has been found that certain structural characteristics of the cyclic peptidomimetic, i.e., the ring size of the cyclic compound and the characteristics of the amino acid residue $A_2$, may affect the biological activity of the conjugate as described hereinbelow.

Examples 8-9 hereinafter show the biological activity of various BTA-conjugates comprising cyclic peptidomimetics of the general formula II with different ring size. The ring size of the cyclic peptidomimetic was altered by changing two structural parameters of the cyclic compound, in particular, (i) the amino acid residue linked to the α-carboxyl group of the aspartic acid residue and to the carboxyl group of $A_2$, i.e. the amino acid residue $A_3$; and (ii) the amino acid residue linked via its α-amino group to the backbone C=O and via its α-carboxyl group to the amino acid residue $A_3$, i.e., the amino acid residue $A_2$. In order to study the effect of $A_3$ on the conjugate activity, BTA-conjugates having the same amino acid residues $A_1$ and $A_2$ but different amino acid residue $A_3$, in particular, Dap, Dab, Orn and Lys, having one to four methylene units in the side chain, respectively, were tested. Similarly, in order to study the effect of $A_2$ on the conjugate activity, BTA-conjugates having the same amino acid residues $A_1$ and $A_3$ but different amino acid residue $A_2$, in particular, Phe, Val, D-Phe, Gly and Asp, were tested. As shown in Example 8, the biological activity of the conjugates tested decreased with increasing the ring size of the cyclic peptidomimetic from 20 atoms to 23 atoms, indicating that the optimum ring size is 20 atoms and that larger ring sizes do not fit the binding site of the integrin. Example 9 shows that the biological activity of conjugates with a hydrophobic amino acid residue $A_2$ was higher than that of conjugates which are more polar, possibly due to the hydrophobic interactions with the hydrophobic pocket in the binding site of the integrin, and further suggests that the D configuration does not fit completely to the hydrophobic pocket.

Example 10 shows the competitive binding level of certain conjugates of the present invention to human $\alpha_v\beta_5$ integrin, using an in vitro assay, and specifically demonstrates that conjugates 1, 4, 7, 28 and 41, having quantitatively the same in vitro binding, are more active than conjugates 5 and 11.

Example 11 describes a study in which the accumulation patterns of conjugates 1, 4 and 41 in large breast cancer tumors were monitored from day 1 to 7 post injection. As shown, these conjugates accumulated in the necrotic area of the tumor, indicating that the conjugates of the present invention can be used for diagnostic uses since the detection of necrotic cores is an important prognosis marker in various types of cancer, e.g., breast cancer, and the detection of tumor margins is essential for total removal of the tumor.

Example 12 describes a study in which the accumulation patterns of conjugates 1, 4, and 41 in prostate cancer cells expressing $\alpha_v\beta_3$ integrin were monitored up to 2 days post injection. As shown, the highest fluorescent level was observed in tumor area at 8 to 11-14 hrs after injection, and the conjugate stayed in the tumor for up to 48 hrs in the cases of conjugates 1 and 4, and up to 24 hrs in the case of conjugate 41. As further shown, the accumulation profiles of these conjugates in prostate and ovarian tumors were nearly the same.

Example 13 describes a toxicity study of conjugates 1, 4 and 41, showing that 5 days after injection of said conjugates, at a dose of 50 mg/kg, no evidence of necrosis or inflammation in the liver or in the kidney was observed, suggesting that these conjugates are not toxic at the dose tested.

In view of all the aforesaid, in one embodiment, the payload moiety of the conjugate of the present invention is a moiety of a fluorescent probe such as, without being limited to, BTA, FITC, dansyl, rhodamine, eosin and erythrosine.

In one preferred embodiment, the conjugate of the present invention is a conjugate of the RGD-containing cyclic peptidomimetic of the general formula I and a moiety of a fluorescent probe, wherein said fluorescent probe is BTA, linked directly, i.e., without a spacer, to the amino acid residue $A_1$, X is —NH— and $A_1$ is Dap (herein identified conjugate 2).

In other preferred embodiments, the conjugate of the present invention is a conjugate of the RGD-containing cyclic peptidomimetic of the general formula I and a moiety of a fluorescent probe, wherein said fluorescent probe is BTA, linked directly to $A_1$, X is —NH—R—, and (i) R is a hydrocarbylene derived from ethane, and $A_1$ is Dap, Dab, Orn, or Lys linked through its α- or side chain amino group to the BTA (herein identified conjugates 1, 3, 4, 5 and 6, respectively); (ii) R is a hydrocarbylene derived from propane, n-butane or n-hexane, and $A_1$ is Orn (herein identified conjugates 24, 25 and 26, respectively); or (iii) R is 1,3-dimethylbenzene-1,3-diyl or piperidine-1,4-diyl, and $A_1$ is Orn (herein identified conjugates 15 and 23, respectively).

In further preferred embodiments, the conjugate of the present invention is a conjugate of the RGD-containing cyclic peptidomimetic of the general formula I and a moiety of a fluorescent probe, wherein said fluorescent probe is dansyl, linked directly to $A_1$, X is —NH—R—, and (i) R is a hydrocarbylene derived from ethane, and $A_1$ is Dap, Orn or Lys (herein identified conjugates 19, 18 and 16, respectively); or (ii) R is a hydrocarbylene derived from n-butane, and $A_1$ is Orn (herein identified conjugate 21).

In still further preferred embodiments, the conjugate of the present invention is a conjugate of the RGD-containing cyclic peptidomimetic of the general formula I and a moiety of a fluorescent probe, wherein said fluorescent probe is BTA, linked directly to $A_1$, X is —O—R—, R is a hydrocarbylene derived from ethane, and $A_1$ is Dap or Lys (herein identified conjugates 7 and 8, respectively).

In yet other preferred embodiments, the conjugate of the present invention is a conjugate of the RGD-containing cyclic peptidomimetic of the general formula I and a moiety of a fluorescent probe, wherein said fluorescent probe is BTA, linked via a spacer to $A_1$, X is —NH—R—, R is a hydrocarbylene derived from ethane, $A_1$ is Dap, and the spacer is a moiety of Gly, β-Ala, GABA, Phe, D-Phe, 1-Nal, D-1-Nal or 3-(aminomethyl)benzoic acid, or a residue of 1,2-ethylenediamine or 1,4-diaminobutane (herein identified conjugates 9, 10, 11, 27, 28, 29, 30, 31, 32 and 33, respectively).

In still further preferred embodiments, the conjugate of the present invention is a conjugate of the RGD-containing cyclic peptidomimetic of the general formula I and a moiety of a fluorescent probe, wherein said fluorescent probe is FITC, linked via a spacer to $A_1$, X is —NH—R—, R is a hydrocarbylene derived from ethane, and (i) $A_1$ is Dap, and the spacer is a n-Ala moiety (herein identified conjugate 12); or (ii) $A_1$ is Lys, and the spacer is a moiety of β-Ala or GABA (herein identified conjugates 13 and 14, respectively).

In yet further preferred embodiments, the conjugate of the present invention is a conjugate of the RGD-containing cyclic peptidomimetic of the general formula I and a moiety of a fluorescent probe, wherein said fluorescent probe is dansyl, linked via a spacer to $A_1$, X is —NH—R—, and (i) R is a hydrocarbylene derived from ethane, $A_1$ is Dap or Lys, and the spacer is a Gly moiety (herein identified conjugates 20 and 17, respectively); or (ii) R is a hydrocarbylene derived from n-butane, $A_1$ is Orn, and the spacer is a n-Ala moiety (herein identified conjugate 22).

In other preferred embodiments, the conjugate of the present invention is a conjugate of the RGD-containing cyclic peptidomimetic of the general formula II and a moiety of a fluorescent probe, wherein said fluorescent probe is BTA, linked directly to $A_1$, $A_1$ is Lys, $A_2$ is Phe, Val, D-Phe, Gly or Asp, and $A_3$ is Dap amidated at its C-terminus (herein identified conjugates 41, 42, 43, 44 and 45, respectively).

In further preferred embodiments, the conjugate of the present invention is a conjugate of the RGD-containing cyclic peptidomimetic of the general formula II and a moiety of a fluorescent probe, wherein said fluorescent probe is BTA, linked directly to $A_1$, $A_1$ is Lys, $A_2$ is Phe, and $A_3$ is Dab, Orn or Lys amidated at its C-terminus (herein identified conjugates 46, 47 and 48, respectively).

Photodynamic therapy (PDT) is a non-surgical treatment of tumors in which non-toxic drugs, called photosensitizing agents, are administered along with light to generate cytotoxic reactive oxygen species in situ, which can inactivate cells. Being a binary treatment modality, PDT allows for greater specificity and has the potential of being more selective, yet not less destructive, when compared with commonly used chemotherapy or radiotherapy.

Porphyrins have been employed as the primary photosensitizing agents in clinics. Optimal tissue penetration by light apparently occurs between 650-800 nm. Porfimer sodium (Photofrin®, Axcan Pharma Inc.) is a complex and inseparable mixture of monomers, dimers, and higher oligomers obtained from hematoporphyrin-IX by treatment with acids that has received FDA approval for treatment of esophageal and endobronchial non-small cell lung cancers.

Due to their intense absorption in favorable spectral regions (650-850 nm) and their ready degradation after treatment, chlorophyll and bacteriochlorophyll derivatives have been identified as excellent sensitizers for PDT of tumors and to have superior properties in comparison to porphyrins. In particular, bacteriochlorophylls are of potential advantage compared to the chlorophylls as they show intense near-infrared bands, i.e., at considerably longer wavelengths than chlorophyll derivatives.

Targeting photodynamic reagents for destruction of the tumor vasculature, as opposed to the tumor cells themselves, may offer therapeutic advantages since tumor-cell growth and development critically depend on continuous oxygen and nutrient supply. Furthermore, targeting the tumor vascular endothelial cell (EC) layer is expected to circumvent the poor penetration of tumor stroma by the therapeutic macromolecules. Although tumor blood vessels might be affected by the tumor microenvironment and acquire a tumor associated "signature", they are not malignant and less likely to develop drug resistance. Furthermore, when a targeted antivascular agent is also active against the tumor cells, additional gains in efficacy can be expected. Thus, by combining antivascular properties with antitumor cytotoxic activities in one drug, its efficacy can be expected to increase and the required effective cytotoxic dose may, consequently, decrease.

Selective vascular targeting can rely on the differential susceptibility and consequent response to therapeutic agents of tumor and normal blood vessels. Alternatively, differential endocytosis may promote selective uptake of cytotoxic or other therapeutic agents. The integrins $α_vβ_5$ and $α_vβ_1$ have been identified in expression patterns typical for angiogenic vascular endothelial cells associated, e.g., with tumors.

Different strategies have been pursued to achieve this goal. Circulating peptides, peptidomimetics or antibodies that target specific sites in the vasculature are attractive as carriers for therapeutics and diagnostic agents offering theoretical advantages over such conjugates that directly target tumor cells, mostly situated beyond physiological barriers such as the blood vessel wall.

Chaleix et al. (2003) disclose the synthesis of RGD-porphyrin conjugates as potential candidates for PDT application, in which the unmetalated porphyrin macrocycle is substituted at each of the positions 10, 15, 20 by 4-methylphenyl or acetylatedglucosyloxyphenyl and at position 5 by a residue of a linear RGD-containing peptide linked to the macrocycle via a spacer arm.

In another embodiment, the payload moiety of the conjugate of the present invention is thus a moiety of a photosensitizer such as, without being limited to, a porphyrin, a chlorophyll or a bacteriochlorophyll.

It is an object of the present invention to provide photosensitizer conjugates that specifically target the sensitizer to the tumor vasculature. There are some advantages for vascular photosensitizer targeting over vascular targeting with conventional chemotherapy. First, during accumulation of a targeted conventional drug, it is often active, unless it is a pro-drug, while the targeted photosensitizer is not active until locally illuminated. Second, a targeted conventional drug will bind and act also at undesirable targets presenting the homing address whereas the targeted photosensitizer will be activated only at the relevant illuminated site. Furthermore, PDT with photosensitizers targeted to the neovascular endothelial signatures in tumor may be remarkably selective in inducing photodynamic endothelial cell injury.

Since the integrin $\alpha_v\beta_3$ has been reported to play an important role in tumor metastasis and angiogenesis, which involve growth of new blood vessels from preexisting vasculatures during tumor growth, it may be a viable marker for tumor growth and spread. Therefore, noninvasive imaging methods for visual monitoring of $\alpha_v\beta_3$ integrin expression in real-time provides opportunities for assessing therapeutic intervention as well as for detection of metastasis.

Integrins link the intracellular cytoskeleton of cells with the extracellular matrix by recognizing the RGD motif. RGD peptides interact with the integrin receptor sites, which can initiate cell-signaling processes and influence many different diseases. Thus, the integrin RGD binding site is an attractive pharmaceutical target. The integrin $\alpha_v\beta_3$ has an RGD binding site and peptides or peptidomimetics containing the RGD sequence home to, and act as antagonists of, $\alpha_v\beta_3$ integrin.

In the bifunctional conjugates of the present invention, the homing property is provided by the RGD-containing cyclic peptidomimetic while the PDT effect is provided by the photosensitizer. These conjugates should be able to target the sensitizer to neovessels of primary solid tumors and possibly respective metastases for the purpose of diagnosis and for photodynamic destruction. They can further act as antiangiogenic agents and initiate apoptotic destruction of neo-endothelial and blood exposed tumor cells.

In preferred embodiments, the payload moiety is a porphyrin, a chlorophyll or bacteriochlorophyll derivative that may be metalated or unmetalated and optionally substituted in the periphery by different substituents such as alkyl, aryl, heteroaryl and/or functional groups. These functional groups may be selected from positively charged groups, negatively charged groups, basic groups that are converted to positively charged groups under physiological conditions, and acidic groups that are converted to negatively charged groups under physiological conditions.

The term "a positively charged group" refers to a cation derived from an N-containing group or from an onium group not containing N. Since tumor endothelium is characterized by an increased number of anionic sites, positively charged groups or basic groups that are converted to positively charged groups under physiological conditions may enhance the targeting efficiency of the conjugates of the present invention.

The term "a negatively charged group" refers to an anion derived from an acid and includes carboxylate ($COO^-$), thiocarboxylate ($COS^-$), sulfonate ($SO_3^-$), and phosphonate ($PO_3^{2-}$), and the "acidic group that is converted to a negatively charged group under physiological conditions" includes the carboxylic (—COOH), thio-carboxylic (—COSH), sulfonic (—SO$_3$H) and phosphonic (—PO$_3$H$_2$) acid groups.

In more preferred embodiments, the payload moiety is a chlorophyll or, most preferably, a bacteriochlorophyll derivative that may be a natural or a synthetic non-natural derivative of chlorophyll or bacteriochlorophyll, including compounds in which modifications have been made in the macrocycle, and/or in the periphery and/or the central Mg atom may be absent or it is replaced by other metal atom suitable for the purpose of diagnosis and/or for the purpose of PDT. Examples of such metals include, but are not limited to, Pd, Pt, Co, Ni, Sn, Cu, Zn, Mn, In, Eu, Fe, Au, Al, Gd, Er, Yb, Lu, Ga, Y, Rh, Ru, Si, Ge, Cr, Mo, Re, Tl and Tc and isotopes thereof.

In one particular preferred embodiment, the conjugate of the present invention is a conjugate of the RGD-containing cyclic peptidomimetic of the general formula I and a moiety of a bacteriochlorophyll derivative, wherein said bacteriochlorophyll derivative is Pd-BTA, linked directly to $A_1$, X is —NH—R—, R is a hydrocarbylene derived from ethane and $A_1$ is Dap (herein identified conjugate 34).

In a further embodiment, the payload moiety of the conjugate of the present invention is a chelating agent, i.e., an agent capable of chelating a radionuclide such as technetium-99m ($^{99m}$Tc). Non-limiting examples of such chelating agents include DTPA and DOTA. Such conjugates may be useful as radio imaging and radiotherapeutic agents.

In preferred embodiments, the conjugate of the present invention is a conjugate of the RGD-containing cyclic peptidomimetic of the general formula I and a moiety of a chelating agent, wherein said chelating agent is DTPA or DOTA, linked directly to $A_1$, X is —NH—R—, R is a hydrocarbylene derived from ethane and $A_1$ is Dap (herein identified conjugates 35 and 36, respectively).

Since most of the currently used chemotherapeutic agents are toxic also to normal cells, the development of targeted chemotherapy, i.e., chemotherapeutic drugs specifically targeted to tumor cells, is of high importance. Targeted cytotoxic peptide conjugates are hybrid molecules composed of a peptide carrier, which binds to receptors on tumor cells and a cytotoxic moiety. This approach effectively increases the specificity and efficacy of the cytotoxic agent in chemotherapy, and should decrease toxic side effects as well.

Thus, in still a further embodiment, the payload moiety of the conjugate of the present invention is a cytotoxic agent.

In one preferred embodiment, the cytotoxic agent of the present invention is an anthracycline chemotherapeutic agent. The anthracycline chemotherapeutic agent may be any chemotherapeutic agent of the anthracycline family including doxorubicin (also known as adriamycin), daunorubicin, epirubicin, idarubicin and mitoxantrone. In a more preferred embodiment, the anthracycline chemotherapeutic agent is doxorubicin, which is a quinine-containing anthracycline and is the most widely prescribed and effective chemotherapeutic agent utilized in oncology. Doxorubicin is indicated in a wide range of human malignancies, including tumors of the bladder, stomach, ovary, lung and thyroid, and is one of the most active agents available for treatment of breast cancer and other indications, including acute lymphoblastic and myelogenous leukemias, Hodgkin's and non-Hodgkin's lymphomas, Ewing's and osteogenic bone tumors, soft tissue sarcomas, and pediatric cancers such as neuroblastoma and Wilms' tumors.

In other preferred embodiments, the cytotoxic agent is a mitotic inhibitor such as paclitaxel, currently used for the treatment of patients with lung, ovarian, breast cancer, head and neck cancer, and advanced forms of Kaposi's sarcoma, as well as for the prevention of restenosis, a topoisomerase I inhibitor such as camptothecin, or a topoisomerase II inhibitor such as ellipticine.

In a further aspect, the present invention provides a pharmaceutical composition comprising a conjugate of an RGD-containing cyclic peptidomimetic and a payload moiety as defined above, or a pharmaceutical acceptable salt thereof, and a pharmaceutically acceptable carrier.

In one embodiment, the pharmaceutical composition comprises a conjugate of a cyclic peptidomimetic as defined above, i.e., a cyclic peptidomimetic of the general formula I or II, and a moiety of a fluorescent probe. In preferred embodiments, the pharmaceutical composition comprises a conjugate selected from the group of conjugates consisting of conjugates 1-33 and 41-48 defined above. Such pharmaceutical compositions may be used for diagnostic purposes, preferably, for visualization of organs and tissues, e.g., in methods of vascular-targeted imaging (VTI), more preferably, for diagnosis of tumors.

In another embodiment, the pharmaceutical composition comprises a conjugate of a cyclic peptidomimetic as defined above, i.e., a cyclic peptidomimetic of the general formula I or II, and a moiety of a photosensitizer as defined above. In a preferred embodiment, the pharmaceutical composition comprises a conjugate selected from the group of conjugates consisting of conjugates 34 and 37-40 defined above. Such compositions may be used in photodynamic therapy (PDT). In one embodiment, the pharmaceutical composition is for use in oncology, particularly for PDT of tumors. Any suitable solid tumor is encompassed by the invention, both primary tumors and metastasis, of tumors selected from, but not limited to, from melanoma, colon, breast, lung, prostate, brain or head and neck cancer. In another embodiment, the pharmaceutical composition is for use in non-oncologic diseases, for PDT of non-neoplastic tissue or organ. In one embodiment, the pharmaceutical composition is used for treatment of vascular diseases such as age-related macular degeneration (AMD) or disorders such as obesity by limiting vascular supply to adipose tissue and thus inhibiting its growth.

In a further embodiment, the pharmaceutical composition comprises a conjugate of a cyclic peptidomimetic as defined above, i.e., a cyclic peptidomimetic of the general formula I or II, and a moiety of an agent capable of chelating a radionuclide. In a preferred embodiment, the pharmaceutical composition comprises conjugate 35 or 36 defined above. Such compositions, when labeled with suitable radionuclides, may be used for radio imaging or radiotherapy.

In yet another embodiment, the pharmaceutical composition comprises a conjugate of a cyclic peptidomimetic as defined above, i.e., a cyclic peptidomimetic of the general formula I or II, and a moiety of a cytotoxic agent as defined above. Such compositions may be used for targeted chemotherapy.

The pharmaceutical composition provided by the present invention may be prepared by conventional techniques, e.g., as described in Remington: The Science and Practice of Pharmacy, 19th Ed., 1995. The composition may be in solid, semisolid or liquid form and may further include pharmaceutically acceptable fillers, carriers or diluents, and other inert ingredients and excipients. Furthermore, the pharmaceutical composition can be designed for a slow release of the conjugate. The composition can be administered by any suitable route, e.g. intravenously, orally, parenterally, rectally, or transdermally. The dosage will depend on the state of the patient, and will be determined as deemed appropriate by the practitioner.

The route of administration may be any route, which effectively transports the active compound to the appropriate or desired site of action, the intravenous route being preferred. If a solid carrier is used for oral administration, the preparation may be tabletted, placed in a hard gelatin capsule in powder or pellet form or it can be in the form of a lozenge. If a liquid carrier is used, the preparation may be in the form of a syrup, emulsion or soft gelatin capsule. Tablets, dragees or capsules having talc and/or a carbohydrate carrier or binder or the like are particularly suitable for oral application. Preferable carriers for tablets, dragees or capsules include lactose, cornstarch and/or potato starch.

In still another aspect, the present invention thus relates to use of a conjugate of an RGD-containing cyclic peptidomimetic and a payload moiety as defined above, or a pharmaceutically acceptable salt thereof, for the preparation of a pharmaceutical composition for diagnostic purposes, photodynamic therapy (PDT), radio imaging or radiotherapy, or targeted chemotherapy.

In still a further aspect, the present invention relates to a conjugate of an RGD-containing cyclic peptidomimetic and a payload moiety as defined above, or a pharmaceutically acceptable salt thereof for diagnostic purposes, photodynamic therapy (PDT), radio imaging or radiotherapy, or targeted chemotherapy.

The invention will now be illustrated by the following non-limiting Examples.

EXAMPLES

Materials and Methods (i) Materials. 2-Chlorotritylchloride resin, Fmoc-Asp-O-Allyl, Fmoc-Gly-OH, Fmoc-Arg(Pbf)-OH, Fmoc-β-Ala-OH, Fmoc-GABA-OH, mono Fmoc-diamines, HOBt, PyBOP, HATU and HOAt were purchased from Novabiochem (USA). Fmoc-Dap(Alloc)-OH, Fmoc-Dab(Alloc)-OH and Fmoc-Lys(Alloc)-OH were purchased from Bachem (Switzerland). Fmoc-Orn(Alloc)-OH, 1-Fmoc-4-aminopiperidine hydrochloride and 4-(Boc-aminomethyl)-aniline were purchased from NeoMPS (France). FITC, dansyl chloride, DIEA, DIC, DMBA, diethyldithiocarbamic acid sodium salt, TFE, TIS, TFA, dry DCM and MeOH were purchased from Sigma (USA). Tetrakis (triphenylphosphine) palladium was purchased from Acros (Belgium). DMF, DCM and acetonitrile were purchased from J. T. Baker (USA). DTPA and DOTA were purchased from Macrocyclics (USA).

UV-Vis spectra were obtained using a Shimadzu 1240 UV-Vis spectrophotometer. HPLC MS analysis was obtained using an Agilent 1100 HPLC equipped with an YMC Pro-RP-C18 reverse phase column, connected to an Applied Biosystems 150EX single-quad mass spectrometer. HPLC analyses were conducted (unless noted otherwise) at standard conditions: 20-95% acetonitrile in water (pH=4.5, maintained by acetic acid) gradient over 30 minutes, at a flow rate of 0.2 ml/min. Preparative HPLC was performed using Waters Delta Prep 4000 system equipped with a Waters 486 UV-VIS tunable absorbance detector and Waters fraction collector, controlled by Millenium v3.05 program. The flow rate was set to 75 ml/min, using a preparative column (Vydac C18, 218TP101550, 50×250 mm, 10-15 μm). Solvents used in the HPLC purification were Solvent A (50 mM solution of ammonium acetate in $H_2O$) and Solvent B (acetonitrile). ELISA plates were read on a Thermo Labsystems Multiscan Spectrum instrument. Fluorescent imaging was carried out using a Xenogen IVIS® 100 Series Imaging System (Alameda, Calif.).

(ii) General procedure for the coupling of mono Fmoc-diamine to H-Arg(Pbf)-Gly-Asp($^\alpha$O-Ally)-2-chlorotrityl resin. Mono Fmoc-diamine hydrochloride (1.05 mmol) was dissolved in DCM (10 ml). DIEA (1.26 mmol) was added to the solution and stirred for 1 min followed by addition of BTC (0.35 mmol) and DIEA (3.15 mmol). The solution obtained was added to 0.21 mmol peptidyl-resin, pre-washed with DCM, and was allowed to react for 1 hr. After coupling, the resin was washed with DCM (3×6 ml, 1 min each) and DMF (6×6 ml, 1 min each). Coupling completion was monitored by qualitative ninhydrin test (Kaiser Test).

(iii) General procedure for the coupling of BTA or Pd-BTA to peptidyl-resin. BTA (0.42 mmol), PyBOP (0.42 mmol) and HOBt (0.42 mmol) were dissolved in DMF (10 ml), and DIEA (1.89 mmol) was then added to the solution and stirred for 5 min. The solution obtained was added to 0.21 mmol peptidyl-resin and was shaken for 2 hrs under argon. After coupling, the resin was washed with DMF (6-8×6 ml, 1 min). Coupling completion was monitored by qualitative ninhydrin test. The coupling of Pd-BTA to the cyclic peptidyl resin was performed under the same coupling conditions as described for BTA.

(iv) General procedure for the coupling of FITC to peptidyl-resin. A solution of FITC (0.63 mmol) in DMF (5 ml) was added to 0.21 mmol peptidyl-resin and was shaken for 1.5 hrs. After coupling, the resin was washed with DMF (6×6 ml, 1 min each). Coupling completion was monitored by qualitative ninhydrin test.

(v) General procedure for the coupling of dansyl chloride to peptidyl-resin. A solution of dansyl chloride (1.05 mmol) and DIEA (1.47 mmol) in DCM (5 ml) was added to 0.21 mmol peptidyl-resin, pre-washed with DCM, and was allowed to react for 1 hr. After coupling, the resin was washed with DCM (5×5 ml, 1 min) and DMF (2×5 ml, 1 min). Coupling completion was monitored by qualitative ninhydrin test.

(vi) Preparation of protected dipeptide Fmoc-Arg(Pbf)-Gly-OH, a building block for the peptide synthesis. A solution of Fmoc-Gly-OH (4.162 gr; 14 mmol) and DIEA (9.755 gr; 56 mmol) in dry DCM (100 ml) was stirred with 10 gr of 2-chlorotrityl chloride resin (substitution 1.4 mmol/gr) for 1 hr at RT. The mixture was transferred to a reactor equipped with a sintered glass bottom and the resin was washed with DCM/MeOH/DIEA (17:2:1) (3×100 ml), DCM (3×100 ml), DMF (3×100 ml), DCM (2×100 ml), MeOH (2×100 ml) and DMF/DCM (1:1) (3×100 ml). Fmoc-group was removed by treatment with 5% piperidine in DMF/DCM (1:1) (100 ml, 10 min), followed by 20% piperidine in DMF (100 ml, 5 min and 2×15 min) and washing the resin with DMF (7×100 ml). Fmoc-Arg(Pbf)-OH (18.17 gr; 28 mmol) in DMF (130 ml) was activated with DIC (4.34 ml; 28 mmol) and HOBt (4.29 gr; 28 mmol) for 15 min at RT and was added to the reaction vessel. The mixture was shaken for 2 hrs at RT. The peptidyl-resin was washed with DMF (5×100 ml), DCM (3×100 ml), MeOH (2×100 ml) and DCM (3×100 ml), and was dried in vacuum for 3 hrs. The protected dipeptide was cleaved from the resin by stirring with a solution of AcOH/TFE/DCM (1:1:3) (250 ml) for 1 hr at RT. The resin was filtered and washed with the same solution (3×50 ml). The combined filtrates were mixed with n-hexane to remove AcOH as an azeotrope and were evaporated to give an oily residue, which solidified upon treatment with cold ether (11). Filtration and washing with cold ether (150 ml) afforded a white powder (8.64 g; 87.5%) with homogeneity of about 99% (HPLC). $C_{36}H_{43}N_5O_3S$. MS (LC-MS) calculated m/z=705.84. Found: 706.30 (M+H). The product was used without further purification.

(vii) General procedure for the cleavage of the peptide conjugate from the resin. After conjugation, the peptidyl-resin was washed with DMF (5×3 ml) and DCM (5×3 ml), and was then dried under reduced pressure for 3 hrs. The peptide conjugate was cleaved from the resin using a cleavage cocktail of TFA/thioanisole/$H_2O$/TIS (85:5:5:5) (6 ml) for 5 min at 0° C. and then for 1 hr at RT. The resin was filtered and washed with the same cleavage cocktail (4 ml). The combined filtrates were evaporated by a stream of $N_2$ to about half of the volume, and the peptide was precipitated by addition of cold ether (25 ml). Centrifugation and decantation of ether layer and additional treatment with cold ether (2×25 ml) afforded the unprotected peptide that was dried in vacuum for 6 hrs. The crude product was purified by RP-HPLC.

(viii) Integrin binding test by ELISA. Nunc immuno-module strips (Nunclon, Cat#167008, Daniel Biotech, Israel) were coated for overnight with 2 μg/ml human integrin $\alpha_v\beta_3$ (Chemicon, Cat#CC1020, Biotest, Israel) dissolved in 0.06 M carbonate-bicarbonate buffer. Strips were blocked for 2 hrs at RT with 2% bovine serum albumin (BSA) (Sigma, Cat#A-9647, Israel) in phosphate buffered saline (PBS) (Biological Industries, Israel). A mixture of c[RGDfK]-biotin ($10^{-3}$M) and a test compound at different concentrations ($10^{-2}$, $10^{-3}$, $10^{-4}$ and $10^{-5}$M) diluted in assay buffer (50 mM Tris HCl, pH=7.7, 0.5% BSA, 0.15 M NaCl, 0.01% Tween 20) was added to the coated strips and was incubated overnight at RT with shaking. After washing with PBS, anti-biotin antibodies labeled by alkaline phosphatase (1:200) (Miltenyi Biotec, Almog, Israel) were added and incubated for 1 hr at RT. The samples were incubated with p-nitrophenyl phosphate substrate (p-NPP, Calbiochem, Mercury, Israel) and read at 405 nm.

(ix) In-vivo ovarian carcinoma model. Female CD-1 nude mice (7-9 weeks old, 23-28 gr) were anaesthetized and subcutaneously (SC) implanted with MLS human ovarian carcinoma cells (obtained from Prof. M. Neeman, the Weizmann Institute of Science, Israel) suspension (2-3×$10^6$ cells/mouse). Tumors reached treatment size, diameter 6-8 mm, within 2-3 weeks.

Animals were anaesthetized by gas with mixture of 7:3 $N_2O$:$O_2$ containing 2% isofluorane (Medeva, Bethlehem, Pa.) or by intraperitoneal (IP) injection with mixture of 5 mg/kg ketamine (Rhone Merieux, Lyon, France) and 1 mg/kg pompun (Bayer, Leverkusen, Germany) (85:15, v:v).

(x) In-vivo colon carcinoma model. This model is similar to the in vivo ovarian carcinoma model described in (ix) above, except for the fact that HT29 human colon carcinoma cells (ATCC, USA, 2-3×$10^6$ cells/mouse) were used instead of MLS human ovarian carcinoma cells.

(xi) In-vivo prostate cancer model. LNCaP cells (3×$10^6$ cells/mouse) were SC implanted on back of severe combined immunodeficiency (SCID) mice. Tumors were allowed to grow for 60-70 days. When tumor reaches the treatment size (0.7-0.8 $cm^3$), the animals were anaesthetized and the test compound solution was intravenously (IV) injected. The images on IVIS were taken at 8, 11, 14, 24 and 48 hrs after injection.

(xii) In-vivo breast cancer model. Female CD-1 nude mice (6-8 weeks old, 20-25 g, obtained from Harlan Biotech Israel, Rehovot, Israel) were implanted with MDA-MB-23'-RFP human breast cancer cells (4×$10^6$ cells/mouse). These cells are, in fact, MDA-MB-231 human breast cancer cells (ATCC, USA) transfected with red fluorescence protein (RFP) gene thus possessing red fluorescence. When tumors reached the size of 1-1.5 $cm^3$ for necrotic tumors, mice were anaesthetized by IP injection of 30 μl mixture of 85:15 ketamine: xylazine, and the test conjugate (15 mg/kg) was then injected to the tail vein.

(xiii) Fluorescent imaging protocol for BTA-RGD conjugates. Test compounds (8 mg/kg) were injected into the tail vein of IP anaesthetized tumor-bearing mice. Images of gas-anaesthetized animals were taken at 6, 8, 10, 12, 14 and 24 hrs (in some cases also at 48 and 72 hrs) after injection using IVIS® 100 Series Imaging System. The excitation and emission filters were set in the IVIS to 710-760 nm and to 810-860 nm, respectively. The emission filter with wavelength closest to the emission peak of the compound was selected among available filters in the standard configuration of IVIS.

(xiv) Fluorescent imaging protocol for FITC-RGD conjugates. Test compounds (8 mg/kg) were injected into the tail vein of IP anaesthetized tumor-bearing mice. Images of gas-anaesthetized animals were taken at 6 and 8 hrs after injection. Animals were sacrificed at 8 hrs, the organs (tumor, kidney, liver) were excited and images of the organs were taken using IVIS® 100 Series Imaging System. The excitation and emission filters were set in the IVIS to 445-490 nm and to 515-575 nm, respectively. The emission filter with wavelength closest to the emission peak of FITC was selected among available filters in the standard configuration of IVIS.

(xv) In-vitro binding assay. MLS human ovarian carcinoma cells were cultured as monolayers in minimum essential medium (MEM-alpha) containing 1 g/l D-glucose, pH 7.4, 10% fetal calf serum (FCS), glutamine (2 mM), penicillin (0.06 mg/ml) and streptomycin (0.1 mg/ml), and were grown at 37° C. in 5% $CO_2$-humidified atmosphere. At 48 hrs before experiment, cells were seeded at 6 well plates ($3 \times 10^5$ cells/well).

Expression of $\alpha_v\beta_3$ integrin on MLS cells. The cells were grown on cover slips. Following overnight serum starvation, fixation with 4% paraformaldehyde (Sigma, Israel) and permeabilization with 0.2% Triton X-100 (Sigma, Israel), cells were incubated in blocking solution (10% of horse serum) (Biological Industries, Israel) for 1 hr at RT. Cells were then incubated with mouse anti-human $\alpha_v\beta_3$ integrin antibodies (1:100) (Chemicon, Biotest, Israel) for 1 hr at RT. Secondary rabbit FITC-labeled anti-mouse IgG (1:200) (Sigma, Israel) were applied to cells for 1 hr at RT. Imaging was performed by fluorescent microscope (Nikon Optiphot2, Japan) equipped with a digital camera (DVC Company, Inc., Austin, Tex.).

In vitro binding assay. RGD-conjugates were initially dissolved in DMSO to yields $4 \times 10^{-3}$ M. The stock solutions were then diluted 1:40 in culture medium and added into MILS or HT29 cells (100 μM/well). Cells were incubated at 37° C. in 5% $CO_2$-humidified atmosphere for 3 hrs. Cells were then washed 3 times with PBS and images were performed on a Xenogen IVIS® 100 Series Imaging System. The excitation and emission filters set in the IVIS for BTA-RGD were 710-760 nm and 810-860 nm, respectively, and for FITC-RGD were 445-490 nm and 515-575 nm, respectively.

(xvi) Competitive binding experiments (determination of $IC_{50}$). Immuno-module strips MAXISORP (Nunc, Danyel Biotech, Israel) were coated with 50 μl/well of 2 μg/ml human $\alpha_v\beta_3$ integrin (Chemicon, USA) overnight and blocked with 2% BSA (Sigma, Israel) for 2 hrs at RT. After wash with Tris buffered saline-Tween (TBST) buffer, a mixture of RGD peptide c[RGDfK]-biotin ($10^{-3}$ M) and the tested RGD-conjugate at different concentrations ($10^{-2}$, $10^{-3}$, $10^{-4}$ and $10^{-5}$ M) was added in triplicates and was incubated overnight and shaken at RT. After wash with PBS buffer, anti-biotin antibodies labeled by alkaline phosphatase (1:200) (Miltenyi Biotec, Germany) were added and incubated for 1 hr at RT. The samples were incubated with p-NPP substrate and read at 405 nm on Multiscan Spectrum (Labotal, Israel). The data were plotted to graph of dependence of binding percent out of concentration of RGD-conjugate and $IC_{50}$ value was determined.

Example 1

Synthesis of Conjugates Based on RGD-Containing Cyclic Peptidomimetics of the General Formula I 1(i) Synthesis of BTA- and Pd-BTA-Cyclic Peptidomimetic Conjugates Herein Identified Conjugates 1, 3-6, 15, 23-26 and 34-Method A Tripeptide Fmoc-Arg(Pbf)-Gly-Asp($^\alpha$O-Allyl)-2-chlorotrityl resin was prepared on a solid phase by coupling of Fmoc-Arg(Pbf)-Gly-OH to resin bound H-Asp-O-Allyl residue.

Attachment of the first amino acid was performed by stirring 2-chlorotrityl chloride resin (300 mg, substitution 1.4 mmol/gr) with a solution of Fmoc-Asp-O-Allyl (83 mg, 0.21 mmol) and DIEA (147 μl, 0.84 mmol) in 5 ml dry DCM for 1 hr at RT to give a loading of about 0.7 mmol/g. Upon coupling completion, the resin was treated (washes and Fmoc-removal) as described in Materials and Methods with corresponding volumes of solvents and reagents solution. Fmoc-Arg(Pbf)-Gly-OH (223 mg, 0.315 mmol), HOBt (48 mg, 0.315 mmol) and DIC (49 μl, 0.315 mmol) were dissolved in 5 ml DMF and stirred at RT for 20 min. The resulting solution was added to the washed H-Asp-O-Allyl-resin and the mixture was shaken for 2 hrs at RT. The peptidyl-resin was washed with DMF ($5 \times 5$ ml). Removal of Fmoc group was carried out by addition of 20% piperidine (5 ml) in DMF ($2 \times 15$ min) followed by DMF wash ($7 \times 5$ ml, 1 min). The coupling of mono Fmoc-diamine was performed as described in Materials and Methods followed by Fmoc deprotection and DMF wash. Coupling of Fmoc-Lys(Alloc)-OH, as well as of Fmoc-Dap(Alloc)-OH, Fmoc-Dab(Alloc)-OH and Fmoc-Orn(Alloc)-OH, to the tetra-peptide was performed by addition of a DMF solution (5 ml) of Fmoc-Lys(Alloc)-OH (0.63 mmol), pre-activated (for 15 min) with HOBt (0.63 mmol) and DIC (0.63 mmol), and coupling time of 1 hr. After coupling, the resin was washed with DMF ($6 \times 5$ ml, 1 min). Coupling completion was monitored by qualitative ninhydrin test (Kaiser Test). Allyl and Alloc deprotection took place by stirring the peptidyl-resin with a solution of $[(C_6H_5)_3P]_4Pd^0$ (0.252 mmol) and DMBA (3.57 mmol) in DCM (5 ml) for 2 hrs at RT under argon. The resin was washed with DCM ($3 \times 5$ ml, 1 min), DMF ($3 \times 5$ ml, 1 min), diethyldithiocarbamic acid sodium salt (0.5% in DMF, $4 \times 5$ ml, 2 min) and finally with DMF ($5 \times 5$ ml, 1 min). On-resin cyclization was done by using a solution of PyBOP (0.63 mmol) and DIEA (1.26 mmol) in DMF (4 ml) for 2 hrs at RT. After Fmoc deprotection, conjugation of BTA to the unprotected peptidyl-resin, as well as cleavage of the peptide from the resin, were performed as described in Materials and Methods. The products were purified by RP-HPLC.

1(ii) Synthesis of the BTA-Cyclic Peptidomimetic Conjugate Herein Identified Conjugate 2-Method B The synthesis of H-Arg(Pbf)-Gly-Asp($^\alpha$-Allyl)-2-chlorotrityl resin was carried out as described above for Method A.

Coupling of Fmoc-NH—$NH_2$ hydrochloride to the unprotected tripeptide. Mono Fmoc-hydrazine hydrochloride (1.05 mmol) was dissolved in a 1:1 mixture of dioxane and 1,3-dichloropropane (10 ml). DIEA (1.26 mmol) was added to this solution and was stirred for 1 minute followed by addition of BTC (0.35 mmol) and DIEA (3.15 mmol). The solution was added to the peptidyl-resin (0.21 mmol) (prewashed with 1:1 dioxane: 1,3-dichloropropane) and was allowed to react for 1 hr at 55° C. After coupling, the resin was washed with DCM (3×6 ml, 1 min) followed by DMF (6×6 ml, 1 min). Coupling completion was monitored by qualitative ninhydrin test (Kaiser Test). The rest of the synthesis was as described for Method A. The product was purified by RP-HPLC.

1(iii) Synthesis of the BTA-Cyclic Peptidomimetic Conjugates Herein Identified Conjugates 9-11 and 27-33-Method C The synthesis of the cyclopentapeptide was carried out as described above for Method A.

Coupling of the amino acid spacers to the cyclopentapeptide. Fmoc amino acid (0.63 mmol of Fmoc-Gly-OH, Fmoc-β-Ala-OH, Fmoc-GABA-OH, Fmoc-Phe-OH, Fmoc-D-Phe-OH, Fmoc-1-Nal-OH, Fmoc-D-1-Nal-OH or Fmoc-3-aminomethylbenzoic acid) was dissolved in DMF (5 ml) and HOBt (0.63 mmol) and DIC (0.63 mmol) were then added and allowed to react for 15 min. The solution was added to the Fmoc-deprotected cyclopentapeptide-2-chlorotrityl resin (0.21 mmol) and was shaken for 1 hr. The resin was washed with DMF (6×5 ml, 1 min) followed by Fmoc deprotection. Coupling of BTA and cleavage of the peptide from the resin were performed as described in Materials and Methods. The products were purified by RP-HPLC.

Coupling of the diamines spacers to the cyclopentapeptide. Mono Fmoc-diamine hydrochloride (1.05 mmol Fmoc-ethylenediamine hydrochloride or Fmoc-diaminobutane hydrochloride) was dissolved in DCM (10 ml). DIEA (1.26 mmol) was added to the solution and stirred for 1 min followed by addition of BTC (0.35 mmol) and DIEA (3.15 mmol). The solution obtained was added to 0.21 mmol peptidyl-resin, pre-washed with DCM, and was allowed to react for 1 hr. After coupling, the resin was washed with DCM (3×6 ml, 1 min each) and DMF (6×6 ml, 1 min each). Coupling completion was monitored by qualitative ninhydrin test (Kaiser Test). Coupling of BTA and cleavage of the peptide from the resin were performed as described in Materials and Methods. The products were purified by RP-HPLC.

1(iv) Synthesis of the BTA-Cyclic Peptidomimetic Conjugates Herein Identified Conjugates 7 and 8-Method D The synthesis of H-Arg(Pbf)-Gly-Asp($^\alpha$O-Allyl)-2-chlorotrityl resin was carried out as described above for Method A.

Coupling of Fmoc-Glycinol to the Fmoc-deprotected tripeptide. Fmoc-Glycinol (1.05 mmol) was dissolved in DCM (10 ml), and BTC (0.35 mmol) was then added to this solution followed by addition of DIEA (3.15 mmol). After stirring for 5 min, the solution obtained was added to peptidyl-resin (0.21 mmol) pre-washed with DCM and allowed to react for 1 hr at RT. The resin was washed with DCM (3×6 ml, 1 min) and DMF (6×6 ml 1 min). Coupling completion was monitored by qualitative ninhydrin test (Kaiser Test). The rest of the synthesis was carried out as described for Method A. Cleavage of the peptide conjugate from the resin was performed with TFA solution (6 ml) containing 15% DCM+5% TIS and 5% thioanisole. The products were purified by RP-HPLC.

1(v) Synthesis of FITC-Cyclic Peptidomimetic Conjugates Herein Identified Conjugates 12-14-Method E The synthesis of cyclopentapeptide was carried out as described above for Method A. After Fmoc deprotection, a solution of Fmoc-β-Ala-OH or Fmoc-GABA-OH (0.63 mmol), HOBt (0.63 mmol) and DIC (0.63 mmol) in DMF (5 ml) was mixed for 15 min, was added to the peptidyl-resin (0.21 mmol) and was allowed to react for 1 hr. The resin was washed with DMF (6×5 ml, 1 min). Removal of Fmoc group was carried out by addition of 20% piperidine in DMF (2×15 ml, 15 min) followed by DMF wash (6×5 ml, 1 min). The coupling of FITC to the unprotected peptidyl-resin and cleavage of the peptide from the resin were performed as described in Materials and Methods. The products were purified by RP-HPLC.

1(vi) Synthesis of Dansyl-Cyclic Peptidomimetic Conjugates Herein Identified Conjugates 16-22-Method F The synthesis of cyclic peptide was carried out as described above for Method A, and after Fmoc-deprotection, the compounds were directly reacted with dansyl chloride as described in Materials and Methods.

Compounds containing a spacer were reacted first with Fmoc-Gly-OH or, alternatively, with Fmoc-β-Ala-OH, under the same conditions as described for Method E, followed by coupling with dansyl chloride. Cleavage of the peptide from the resin was performed as described in Materials and Methods. The products were purified by RP-HPLC.

1(vii) Synthesis of the DTPA-Cyclic Peptidomimetic Conjugate Herein Identified Conjugate 35-Method G The synthesis of cyclic peptide was carried out as described above for Method A. After Fmoc-deprotection, a solution of DTPA-tetra (t-Bu ester) (0.42 mmol) in DMF (3 ml) activated by HATU (0.42 mmol), HOAt (0.42 mmol) and DIEA (0.42 mmol) was added to the peptidyl resin (0.14 mmol) and shaken for 2 hrs at RT. The resin was washed with DMF (4 ml, 5 times, 1 min each time). Cleavage of the peptide from the resin was performed as described in Materials and Methods.

1(viii) Synthesis of the DOTA-Cyclic Peptidomimetic Conjugate Herein Identified Conjugate 36-Method H The synthesis of cyclic peptide was carried out as described above for Method A. After Fmoc-deprotection, a solution of DOTA-tris (t-Bu ester) (0.42 mmol) in DMF (3 ml) activated by HATU (0.42 mmol), HOAt (0.42 mmol) and DIEA (0.42 mmol) was added to the peptidyl resin (0.14 mmol) and shaken for 3 hrs at 60° C. The resin was washed with DMF (4 ml, 5×1 min). Cleavage of the peptide from the resin was performed as described in Materials and Methods.

Table 1 lists the conjugates synthesized and the structural characteristics thereof.

TABLE 1

Conjugates based on cyclic peptidomimetics of the general formula I synthesized and method of synthesis

| Conjugate | X* | R* | A₁* | Spacer | Payload | Method | MW |
|---|---|---|---|---|---|---|---|
| 1 | NHR | (CH₂)₂ | Dap | — | BTA | A | 1217.3 |
| 2 | NH | — | Dap | — | BTA | B | 1189.8 |
| 3 | NHR | (CH₂)₂ | Dab | — | BTA | A | 1231.3 |
| 4 | NHR | (CH₂)₂ | Orn | — | BTA | A | 1245.3 |
| 5 | NHR | (CH₂)₂ | Lys | — | BTA | A | 1259.4 |
| 6 | NHR | (CH₂)₂ | Lys | — | BTA | A | 1259.4 |
| 7 | OR | (CH₂)₂ | Dap | — | BTA | D | 1218.2 |
| 8 | OR | (CH₂)₂ | Lys | — | BTA | D | 1260.3 |
| 9 | NHR | (CH₂)₂ | Dap | Gly moiety | BTA | C | 1275.2 |
| 10 | NHR | (CH₂)₂ | Dap | β-Ala moiety | BTA | C | 1289.2 |
| 11 | NHR | (CH₂)₂ | Dap | GABA moiety | BTA | C | 1303.2 |
| 12 | NHR | (CH₂)₂ | Dap | β-Ala moiety | FITC | E | 960.7 |
| 13 | NHR | (CH₂)₂ | Lys | β-Ala moiety | FITC | E | 1002.7 |
| 14 | NHR | (CH₂)₂ | Lys | GABA moiety | FITC | E | 1016.7 |
| 15 | NHR | 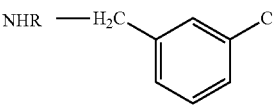 | Orn | — | BTA | A | 1321.2 |
| 16 | NHR | (CH₂)₂ | Lys | — | Dansyl | F | 776.3 |
| 17 | NHR | (CH₂)₂ | Lys | Gly moiety | Dansyl | F | 833.6 |
| 18 | NHR | (CH₂)₂ | Orn | — | Dansyl | F | 762.3 |
| 19 | NHR | (CH₂)₂ | Dap | — | Dansyl | F | 734.3 |
| 20 | NHR | (CH₂)₂ | Dap | Gly moiety | Dansyl | F | 791.5 |
| 21 | NHR | (CH₂)₄ | Orn | — | Dansyl | F | 789.7 |
| 22 | NHR | (CH₂)₄ | Orn | β-Ala moiety | Dansyl | F | 860.72 |
| 23** | NHR |  | Orn | — | BTA | A | 1285.4 |
| 24 | NHR | (CH₂)₃ | Orn | — | BTA | A | 1259.8 |
| 25 | NHR | (CH₂)₄ | Orn | — | BTA | A | 1273.4 |
| 26 | NHR | (CH₂)₆ | Orn | — | BTA | A | 1301.4 |
| 27 | NHR | (CH₂)₂ | Dap | Phe moiety | BTA | C | 1364.4 |
| 28 | NHR | (CH₂)₂ | Dap | D-Phe moiety | BTA | C | 1364.4 |
| 29 | NHR | (CH₂)₂ | Dap | 1-Nal moiety | BTA | C | 1414.4 |
| 30 | NHR | (CH₂)₂ | Dap | D-1-Nal moiety | BTA | C | 1414.4 |
| 31 | NHR | (CH₂)₂ | Dap | 3-(aminomethyl) benzoic acid moiety | BTA | C | 1350.4 |
| 32 | NHR | (CH₂)₂ | Dap | —HN—(CH₂)₂—NH— | BTA | C | 1304.2 |
| 33 | NHR | (CH₂)₂ | Dap | —HN—(CH₂)₄—NH— | BTA | C | 1332.2 |
| 34 | NHR | (CH₂)₂ | Dap | — | Pd-BTA | A | 1321.3 |
| 35 | NHR | (CH₂)₂ | Dap | — | DTPA | G | 875.0 |
| 36 | NHR | (CH₂)₂ | Dap | — | DOTA | H | 887.0 |

*X, R and A₁ are defined according to the definitions of the general formula I.
**R together with the nitrogen atom attached thereto form a saturated heterocyclic ring.

Example 2

Synthesis of BTA-Conjugates Based on RGD-Containing Cyclic Peptidomimetics of the General Formula II In a reaction vessel equipped with a sintered glass bottom, rink amide MBHA resin (300 mg, substitution 0.58 mmol/g) was swelled in DMF by agitation overnight. The Fmoc group was removed from the resin upon treatment with 20% piperidine in DMF for 15 min (3 ml). This action was repeated twice. The resin was washed with DMF (4 ml, 2 min, 5 times). Coupling of Fmoc-Dap(Alloc)-OH, as well as of Fmoc-Dab(Alloc)-OH, Fmoc-Orn(Alloc)-OH and Fmoc-Lys(Alloc)-OH, to the resin was performed by addition of a DMF solution (2.5 ml) of Fmoc-Dap(Alloc)-OH (0.52 mmol), preactivated (for 15 min) with HOBt (0.52 mmol) and DIC (0.52 mmol), and coupling time 1 hr. After coupling, the resin was washed with DMF (4 ml, 2 min, 5 times). Coupling completion was monitored by qualitative ninhydrin test (Kaiser Test). Fmoc removal and DMF wash after Fmoc deprotection were carried out as described above. Coupling of Fmoc-Asp(O-tBu)-OH, Fmoc-Gly-OH, Fmoc-Arg(Pbf)-OH and Fmoc-Lys(Dde)-OH, and the Fmoc deprotection between each coupling, were performed under the same conditions as described for Fmoc-Dap(Alloc)-OH.

General Procedure for the Coupling of Amino Acid Allyl Ester to the Penta-Peptide Lys(Dde)-Arg(Pbf)-Gly-Asp(O-tBu)-X-Rink Amide Resin Amino acid allyl ester as a TsOH salt (0.87 mmol) was dissolved in DCM (7 ml). DIEA (1.05 mmol) was added to the solution and stirred for 1 min followed by addition of BTC (0.29 mmol) and DIEA (2.6 mmol). The solution obtained was added to 0.174 mmol peptidyl-resin, pre-washed with DCM, and was allowed to react for 1 hr. After coupling, the resin was washed with DCM (3×6 ml, 1 min each) and DMF (6 times×6 ml, 1 min each). Coupling completion was monitored by qualitative ninhydrin test.

After coupling of amino acid allyl ester and DMF wash, the resin was washed with DCM (4 times, 4 ml, 1 min each). Allyl and Alloc deprotection took place by stirring the peptidyl-resin with a solution of $[(C_6H_5)_3P]_4Pd^0$ (0.21 mmol) and DMBA (2.61 mmol) in DCM (5 ml) for 2 hrs at RT under argon. The resin was washed with DCM (3×5 ml, 1 min), DMF (3×5 ml, 1 min), diethyldithiocarbamic acid sodium salt (0.5% in DMF, 4×5 ml, 2 min) and finally with DMF (5×5 ml, 1 min). On-resin cyclization was done by using a solution of PyBOP (0.52 mmol) and DIEA (1.04 mmol) in DMF (4 ml) for 2 hrs at RT. After cyclization, the Dde group was removed by addition of 2% hydrazine monohydrate in DMF (3 times, 3 min each time) followed by DMF wash (4 ml, 6 times, 2 min each time). Conjugation of BTA to the unprotected peptidyl-resin, as well as cleavage of the peptide from the resin, were performed as described in Materials and Methods. The products were purified by RP-HPLC.

Table 2 lists the conjugates synthesized and the structural characteristics thereof.

TABLE 2

Conjugates based on cyclic peptidomimetics of the general formula II synthesized

| Conjugate | $A_1$* | $A_2$* | $A_3$* | Spacer | Payload | MW |
|---|---|---|---|---|---|---|
| 41 | Lys | Phe | Dap | — | BTA | 1449.4 |
| 42 | Lys | Val | Dap | — | BTA | 1401.38 |
| 43 | Lys | D-Phe | Dap | — | BTA | 1449.38 |
| 44 | Lys | Gly | Dap | — | BTA | 1359.33 |
| 45 | Lys | Asp | Dap | — | BTA | 1418.31 |
| 46 | Lys | Phe | Dab | — | BTA | 1463.4 |
| 47 | Lys | Phe | Orn | — | BTA | 1477.4 |
| 48 | Lys | Phe | Lys | — | BTA | 1491.4 |

*$A_1$, $A_2$ and $A_3$ are defined according to the definitions of the general formula II.

Example 3

The Ring Size of a Cyclic Peptidomimetic of the General Formula I Affects the Biological Activity of the Conjugate Based Thereon In order to examine whether the ring size of the RGD-containing cyclic peptidomimetic of the general formula I affects the biological activity of the conjugate, the activity of various fluorescent probe-conjugates based on cyclic peptidomimetics of the general formula I having different ring size was tested in both in vivo ovarian carcinoma model and in vitro binding assay using human ovarian carcinoma cells, as described in Materials and Methods.

The ring size of the RGD-containing cyclic peptidomimetic was changed by altering two structural parameters of the cyclic compound, in particular, (i) the amino acid residue linked by amide bonds via its α- or side-chain carboxyl group to the backbone NH and via its α- or side-chain amino group to the α-carboxyl group of the aspartic acid residue, i.e., radical $A_1$ in the general formula I; and (ii) the radical bridging the backbone carbonyl and the backbone NH, i.e., radical X in the general formula I. The specific amino acid residues used were residues of diaminopropionic acid (Dap), diaminobutyric acid (Dab), ornithine (Orn) and lysine (Lys), having one to four methylene units, respectively, in the side chain; and the different radicals X used were NH, $NH(CH_2)_2$, $NH(CH_2)_3$, $NH(CH_2)_4$ and $NH(CH_2)_6$, which, together with the backbone NH, form a moiety of hydrazine, diaminoethane, diaminopropane, diaminobutane and diaminohexane, respectively, bridging $A_1$ and the backbone carbonyl.

Table 3 shows the various fluorescent probe-conjugates tested and the biological activity thereof. As shown, the activity of the conjugates tested increased with increasing the ring size of the cyclic peptidomimetic from 16 atoms to 18-20 atoms; however, it decreased with further increasing the ring size. These results indicate that whereas the urea bond bridging the α-amino group of the arginine residue and radical X makes the cyclic peptidomimetic more rigid, a larger ring having up to 18-20 atoms is more flexible to adopt the desired conformation for binding to the integrin. On the other hand, in cases wherein the ring size of the cyclic peptidomimetic is higher than 20 atoms, the cyclic peptidomimetic probably cannot adopt the desired conformation for binding to the integrin.

TABLE 3

The biological activity of fluorescent probe-conjugates based on cyclic peptidomimetics of the general formula I having different ring size

| Conjugate | Ring size (atoms) | Ovarian carcinoma model (in vivo) | Integrin binding assay (in vitro) |
|---|---|---|---|
| 2 | 16 | Fluorescence spreads all over the body up to 6 hrs. At 10 hrs, low signal in liver and tumor. Complete clearance at 21 hrs. | No binding |
| 6 | 17 | Fluorescence spreads all over the body up to 6 hrs. At 8 hrs, strong signal in liver. Complete clearance at 15 hrs. | No binding |
| 1 | 18 | Fluorescence spreads all over the body up to 10 hrs with strong signals in liver and tumor. At 24-72 hrs, only in tumor. | Binding |
| 19 | 18 | At 8 hrs, strong accumulation in tumor but not in kidney or liver. | |
| 3 | 19 | Fluorescence spreads all over the body during 8 hrs. At 10 hrs, strong signal in liver and tumor. At 14 hrs, only in tumor. Most of the drug is cleared at 23 hrs. | No binding |
| 4 | 20 | Fluorescence spreads all over the body during 8 hrs. At 10 hrs, strong signal in liver and tumor. At 14 hrs, only in tumor. Most of the drug is cleared at 23 hrs. | Binding |
| 18 | 20 | At 8 hrs, strong accumulation in tumor but not in kidney or liver. | |
| 5 | 21 | Fluorescence spreads all over the body up to 8 hrs with high spots in liver and tumor. At 10 rsh, only in liver and tumor. At 12-23 hrs, only in tumor. | Binding |
| 16 | 21 | At 8 hrs, strong accumulation in tumor but weak in kidney and liver. | |
| 24 | 21 | Accumulation in tumor and liver up to 14 hrs with maximum level at 11 hrs. Complete clearance at 48 hrs. | Weak binding |
| 25 | 22 | Accumulation in tumor up to 28 hrs with maximum level at 8-11 hrs. Complete clearance at 48 hrs. | Weak binding |
| 21 | 22 | At 8 hrs, strong accumulation in tumor but not in kidney or liver. | |
| 26 | 24 | Accumulation in tumor and liver up to 14 hrs with maximum level at 8 hrs. Complete clearance at 24 hrs. | No binding |

* The characterization of each conjugate is presented in Table 1 hereinbefore.

Example 4

The Size and Structure of the Diamine Residue in a Cyclic Peptidomimetic of the General Formula I Affects the Biological Activity of the Conjugate Based Thereon In order to examine whether the size and structure of the diamine residue, linked by amide bonds to either the α- or side-chain carboxyl group of the amino acid residue $A_1$ in the general formula I and, via the backbone carbonyl, to the α-amino group of the arginine residue, affects the biological activity of the conjugate, the activity of various BTA-conjugates based on cyclic peptidomimetics of the general formula I having different diamine residues as defined above was tested in both in vivo ovarian carcinoma model and in vitro binding assay using human ovarian carcinoma cells, as described in Materials and Methods.

The specific conjugates tested were conjugates 4, 24, 25, 15 and 23, in which the amino acid residue $A_1$ is ornithine; the BTA molecule is linked to the N-terminal of the peptidomimetic ring without a spacer; and the radical designated X in the general formula I is $-NH(CH_2)_{2-4}-$, 1,3-dimethylbenzene-1,3-diyl or piperidine-1,4-diyl, respectively.

Table 4 shows the various conjugates tested and the biological activity thereof. As shown, the biological activity of conjugate 4 was the highest among the conjugates in which alkyldiamine residues are bridging $A_1$ and the backbone C=O, indicating that the biological activity of these conjugates decrease as the length of the alkyl chain increase. Furthermore, when the peptidomimetic ring becomes rigid, as in the cases of conjugates 15 and 23 wherein radicals other than alkyldiamine residues were used, no biological activity was measured, indicating that the peptidomimetic ring in such conjugates adopts a conformation that is undesirable for the interaction with the integrin.

human ovarian carcinoma cells, as described in Materials and Methods. The specific spacers used were moieties of various natural or synthetic amino acids, in particular, glycine, β-alanine, phenylalanine, D-phenylalanine, 1-naphthylalanine (1-Nal), D-1-naphthylalanine (D-1-Nal), γ-aminobutiric acid (GABA) and 3-(aminomethyl)benzoic acid.

Table 5 shows the various conjugates tested and the biological activity thereof. As shown, Conjugate 1 having no spacer between the BTA molecule and the cyclic peptidomimetic showed high biological activity, probably due to the fact that the BTA molecule does not interfere with the binding of the cyclic peptidomimetic to the integrin. Contrary to that, conjugates in which glycine or β-alanine moieties were used as spacers, having an increased distance between the cyclic peptidomimetic and the BTA molecule, showed lower biological activity, probably because of the bulkiness of the BTA molecule. In the case of conjugate 11, in which a GABA moiety was used as a spacer, i.e., the distance between the cyclic peptidomimetic and the BTA molecule was further increased, both in vitro and in vivo results showed high fluorescence, possibly indicating that GABA is long enough for giving more freedom to the peptidomimetic ring to bind to the integrin; however, not too long to cause folding of the BTA molecule over the peptidomimetic ring.

In cases smaller fluorescent probes, i.e., FITC or dansyl, were used, the distance between the fluorescent probe and the

TABLE 4

The biological activity of BTA-conjugates based on cyclic peptidomimetics of the general formula I having different diamine units linking via amide bonds the arginine residue and the amino acid residue designated $A_1$

| Conjugate | Diamine residue | Ovarian carcinoma, model (in vivo) | Integrin binding assay (in vitro) |
|---|---|---|---|
| 4 | $-NH-(CH_2)_2-NH-$ | At 10 hrs, strong signal in liver and tumor. At 14 hrs, only in tumor. Most of the drug is cleared at 23 hrs. | Binding |
| 24 | $-NH-(CH_2)_3-NH-$ | Accumulation in tumor and liver up to 14 hrs with maximum level at 11 hrs. Complete clearance at 48 hrs. | Weak binding |
| 25 | $-NH-(CH_2)_4-NH-$ | Accumulation in tumor up to 28 hrs with maximum level at 8-11 hrs. Complete clearance at 48 h. | Weak binding |
| 15 | HN-CH2-(1,3-phenylene)-CH2-NH | Strong accumulation in tumor up to 24 hrs. | No binding |
| 23 | piperidine-1,4-diyl (—N⟩—NH—) | High fluorescence spreads all over the body up to 48 hrs. | No binding |

* The characterization of each conjugate is presented in Table 1 hereinbefore.

Example 5

The Spacer Linking the Payload Moiety to a Cyclic Peptidomimetic of the General Formula I Affects the Biological Activity of the Conjugate In this experiment, the biological activity of various fluorescent probe-conjugates based on cyclic peptidomimetics of the general formula I having different spacers linking the fluorescent probe moiety and the N-terminal of the cyclic peptidomimetic, i.e., either the α- or side-chain amino group of the amino acid residue $A_1$, was tested in both in vivo ovarian carcinoma model and in vitro binding assay using N-terminal of the peptidomimetic ring had no influence on the biological activity of the conjugate.

Conjugates 27 and 28, in which phenylalanine and D-phenylalanine moieties, respectively, were used as spacers, were more active than conjugate 9, in which a glycine moiety was used as the spacer, probably because of the aromatic side chain of phenylalanine, which provides interaction with the hydrophobic pocket of the integrin. The biological activity of conjugate 28, which was higher than that of conjugate 27 may further indicate that the D configuration of the phenylalanine may fit the hydrophobic pocket of the integrin better than the L configuration, thus improve binding.

Conjugates 32 and 33, in which residues of 1,2-ethylenediamine and 1,4-diaminobutane, respectively, were used as spacers and an urea bond was formed between the peptidomimetic ring and the BTA moiety, had nearly the same biological activity as conjugates 10 and 11, indicating that the urea bond has nearly the same activity as the amide bond and it does not influence the conformation of the peptidomimetic.

TABLE 5

The biological activity of fluorescent probe-conjugates based on cyclic peptidomimetics of the general formula I having different spacers

| Conjugate | Spacer | Ovarian carcinoma model (in vivo) | Integrin binding assay (in vitro) |
|---|---|---|---|
| 1 | — | Fluorescence spreads all over the body up to 10 hrs with strong signals in liver and tumor. At 24-72 hrs, only in tumor. | Binding |
| 19 | — | At 8 hrs, strong accumulation in tumor but not in kidney or liver. | |
| 9 | Gly moiety | Complete clearance at 8 hrs. | Low binding |
| 20 | Gly moiety | At 8 hrs, strong accumulation in tumor but not in kidney or liver. | |
| 10 | β-Ala moiety | Fluorescence spreads all over the body and clears very fast. | No binding |
| 12 | β-Ala moiety | At 8 hrs, accumulation in tumor and kidney. | Binding |
| 11 | GABA moiety | Fluorescence spreads all over the body up to 12 hrs with strong signals in liver and tumor. At 24 hrs, mainly in tumor. | Strong binding |
| 27 | Phe moiety | At 8-14 hrs, only in tumor. Complete clearance at 24 hrs. | Weak binding |
| 28 | D-Phe moiety | At 8-24 hrs, only in tumor. Complete clearance at 48 hrs. | Strong binding |
| 16 | — | At 8 hrs, strong accumulation in tumor but weak in kidney and liver. | |
| 17 | Gly moiety | At 8 hrs, strong accumulation in tumor but not in kidney or liver. | |
| 13 | β-Ala moiety | At 8 hrs, accumulation in tumor and in kidney. | Binding |
| 14 | GABA moiety | At 8 hrs, weak accumulation in tumor and strong in kidney. | Binding |
| 29 | 1-Nal moiety | At 8 hrs, accumulation only in tumor and stays there up to 24 hrs. | Weak binding |
| 30 | D-1-Nal moiety | At 24 hrs, accumulation in tumor. Signal from the body is high. | Weak binding |
| 31 | 3-(aminomethyl) benzoic acid moiety | At 8 hrs, accumulation only in tumor and stays there up to 24 hrs. | Weak binding |
| 32 | NH—$(CH_2)_2$—NH | At 24 hrs, accumulation in tumor and stays there for more than 72 hrs. | Weak binding |
| 33 | NH—$(CH_2)_4$—NH | At 24 hrs, accumulation in tumor and stays there for more than 5 days. | Strong binding |

* The characterization of each conjugate is presented in Table 1 hereinbefore.

Example 6

The Biological Activity of Conjugates Based on Cyclic Peptidomimetics of the General Formula I in which an Urea Moiety is Formed with the α-Amino Group of the Arginine Residue is Similar to that of Conjugates in which a Carbamate Moiety is Formed In this experiment, the biological activity of conjugates, in particular BTA-conjugates, based on cyclic peptidomimetics of the general formula I in which an urea moiety is formed with the α-amino group of the arginine residue was compared with that of conjugates in which a carbamate moiety is formed.

The specific conjugates tested were conjugates 1 and 5, in which the amino acid residue $A_1$ in the general formula I is a diaminopropionic acid or lysine residue, respectively; the BTA molecule is linked to the N-terminal of the cyclic peptidomimetic without a spacer; and the radical designated X in the general formula I is —$NH(CH_2)_2$—; and conjugates 7 and 8 having a similar structure wherein the radical designated X is —$O(CH_2)_2$— instead of —$NH(CH_2)_2$—. The biological activity of the conjugates was tested in colon carcinoma model as well as in ovarian carcinoma in both in vivo and in vitro binding assay using human ovarian carcinoma cells, as described in Materials and Methods.

The biological activity of conjugates 1 and 5 in ovarian carcinoma model is described in Table 3. As shown in Table 6, the conjugates in which an urea moiety is formed with the α-amino group of the arginine residue had a similar activity to that of the corresponding conjugates in which a carbamate moiety is formed, indicating that the nature of the moiety formed with the α-amino group of the arginine residue does not affect the biological activity of the conjugate.

TABLE 6

The biological activity of BTA-conjugates based on cyclic peptidomimetics of the general formula I in which an urea vs. a carbamate moiety is formed with the α-amino group of the arginine residue

| Conjugate | Colon/Ovarian carcinoma model (in vivo) | Integrin binding assay (in vitro) |
|---|---|---|
| 1 | Colon-Orthotopic: accumulation in tumor up to 8 hrs. Complete clearance at 12 hrs. | Binding |
| 5 | Colon-SC: fluorescence spreads all over the body during 8 hrs. At 10 hrs, strong signal in liver and tumor. At 14-24 hrs, only in tumor (n = 1); Orthotopic: accumulation in tumor up to 8 hrs. Complete clearance at 12 hrs. | Binding |
| 7 | Colon-fluorescence spreads all over the body up to 8 hrs. At 10-24 hrs, only in tumor. Ovarian-fluorescence spreads all over the body up to 8 hrs. At 10-24 hrs, only in tumor. | Binding |
| 8 | Colon-fluorescence spreads all over the body up to 6 hrs. At 8 hrs, accumulates in tumor and liver. At 12-14 hrs, only in tumor. Almost complete clearance at 24 hrs. Ovarian-fluorescence spreads all over the body up to 6 hrs. At 8 hrs, in tumor and liver. At 14 hrs, only in tumor. Almost complete clearance at 24 hrs. | Binding |

* The characterization of each conjugate is presented in Table 1 hereinbefore.

Example 7

The Biological Activity of BTA Derivative-Conjugates Based on Cyclic Peptidomimetics of the General Formula I in which the Taurine Residue of the BTA is Replaced by Different Diamines is Similar to that of the Corresponding Non-Derivatized Conjugates Four different bacteriochlorophyll derivative-conjugates based on cyclic peptidomimetics of the general formula I, herein identified conjugates 37-40, were synthesized, and their biological activity in MLS human ovarian carcinoma cells was tested using the integrin binding assay. These conjugates were based on conjugates 1 and 4 in which the taurine residue (—NH—$(CH_2)_2$—$SO_3H$) in the BTA moiety was replaced by different nucleophiles, in particular, —NH—(CH$_2$)$_2$—NH$_2$ and —NH—(CH$_2$)$_2$—NH—CH$_3$.

The cyclic peptidomimetic for these conjugates was synthesized according to Method A described above. After cyclization and Dde removal, a solution of Bpheide (2 eq), activated by PyBoP (2 eq), HOBt (2 eq), DIEA (6 eq) in DMF was added to the peptidyl resin and shaken for 2 hrs under argon. The resin was washed with DMF eight times (monitoring by ninhydrin test). A solution of diamine (30 eq) in DMF was added to the peptidyl resin and shaken for 1 hr under argon followed by DMF wash. The peptide was cleaved from the resin as described in Materials and Methods, and the crude conjugates were purified by RP-HPLC. As shown in Table 7, the biological activity of all these conjugates was similar, indicating that in these cases, the amino group has no effect on the biological activity and its behavior is nearly the same as that of the sulphonate in taurin.

TABLE 7

The biological activity of various substituted BTA-conjugates based on cyclic peptidomimetics of the general formula I

| Conjugate | X* | A$_1$* | Spacer | Probe | J* | Integrin binding assay (in vitro) |
|---|---|---|---|---|---|---|
| 1 | NH(CH$_2$)$_2$ | Dap | — | BTA | — | Binding |
| 37 | NH(CH$_2$)$_2$ | Dap | — | Substituted BTA | —NH—(CH$_2$)$_2$—NH$_2$ | Binding |
| 38 | NH(CH$_2$)$_2$ | Dap | — | Substituted BTA | —NH—(CH$_2$)$_2$—NH—CH$_3$ | Binding |
| 39 | NH(CH$_2$)$_2$ | Orn | — | Substituted BTA | —NH—(CH$_2$)$_2$—NH$_2$ | Binding |
| 40 | NH(CH$_2$)$_2$ | Orn | — | Substituted BTA | —NH—(CH$_2$)$_2$—NH—CH$_3$ | Binding |

*X and A$_1$ are defined according to the definitions of the general formula I.
*J represents the specific nucleophile replacing taurine in BTA.

Example 8

The Ring Size of a Cyclic Peptidomimetic of the General Formula II Affects the Biological Activity of the Conjugate Based Thereon In order to examine whether the ring size of the cyclic peptidomimetic of the general formula II affects the biological activity of the conjugate, the activity of various BTA-conjugates based on cyclic peptidomimetics of the general formula II having the same amino acid residues A$_1$ (Lys) and A$_2$ (Phe), but different amino acid residues A$_3$, in particular, Dap, Dab, Orn and Lys, having one to four methylene units, respectively, in the side chain, was tested in both in vivo ovarian carcinoma model and in vitro binding assay using human ovarian carcinoma cells, as described in Materials and Methods.

Table 8 shows the various BTA-conjugates tested and the biological activity thereof. As shown, the biological activity of the conjugates tested decreased with increasing the ring size of the cyclic peptidomimetic from 20 atoms to 23 atoms, indicating that a ring size larger than 20 atoms does not fit the binding site of the integrin.

TABLE 8

The biological activity of BTA-conjugates based on cyclic peptidomimetic of the general formula II having different ring size

| Conjugate | Ring size (No. of atoms) | Ovarian carcinoma model (in vivo) | Integrin binding assay (in vitro) |
|---|---|---|---|
| 41 | 20 | Accumulation in tumor up to 8 hrs. Complete clearance at 12 hrs. | Binding |
| 46 | 21 | | Weak binding |
| 47 | 22 | | Weak binding |
| 48 | 23 | | Weak binding |

* The characterization of each conjugate is presented in Table 2 hereinbefore.

Example 9

The Characteristics of the Amino Acid Residue A$_2$ in a Cyclic Peptidomimetic of the General Formula II Affects the Biological Activity of the Conjugate Based Thereon In order to examine whether the size and the structure of the amino acid residue A$_2$ in the cyclic peptidomimetic of the general formula II, linked via its α-amino group to the backbone C=O and via its α-carboxyl group to the amino acid residue A$_3$, affects the biological activity of the conjugate, the activity of various BTA-conjugates based on cyclic peptidomimetics of the general formula II having the same amino acid residues A$_1$ (Lys) and A$_3$ (Dap), but different amino acid residues A$_2$, in particular, Phe, Val, D-Phe, Gly and Asp, was tested in both in vivo ovarian carcinoma model and in vitro binding assay using human ovarian carcinoma cells, as described in Materials and Methods.

Table 9 shows the various BTA-conjugates tested and the biological activity thereof. As shown, the biological activity of conjugates 41, 42 and 43, having hydrophobic amino acid residues A$_2$, was higher than that of conjugates 44 and 45, which are more polar, possibly due to the hydrophobic interactions with the hydrophobic pocket in the binding site of the integrin. The fact that conjugate 43 was less active than conjugate 41 may be due to the configuration of the former, suggesting that the D configuration does not fit completely to the hydrophobic pocket.

TABLE 9

The biological activity of BTA-conjugates based on cyclic peptidomimetic of the general formula II having different amino acid residues $A_2$

| Conjugate | $A_2$ | Biological activity (ovarian carcinoma) |
|---|---|---|
| 41 | Phe | In vitro: binding<br>In vivo: accumulates in MLS ovarian carcinoma, stays in tumor up to 24 hrs after injection and cleared from the body and from tumor at 48 hrs. Orthotopic: At 11 hrs after injection the high fluorescence is detectable in tumor area ether SC or orthotopic. At 24 hrs the drug was cleared from the body but in tumor area the fluorescent level was still detectable for up to 3 days after injection. Drug accumulation doesn't depend on site of implantation. |
| 42 | Val | In vitro: binding<br>In vivo: This compound accumulates in ovarian and colon tumors at 24 hrs after injection and stays there up to 72 h. |
| 43 | D-Phe | In vitro: weak binding |
| 44 | Gly | In vitro: no binding |
| 45 | Asp | In vitro: no binding |

* The characterization of each conjugate is presented in Table 2 hereinbefore.

Example 10

Competitive Binding of Various BTA-Conjugates of the Present Invention to Human $\alpha_v\beta_3$ Integrin In this study, the competitive binding level, i.e., the $IC_{50}$, of various BTA-conjugates of the present invention to human $\alpha_v\beta_3$ integrin was tested against biotin-c[RGDfK], as described in Material and Methods. The specific conjugates tested were conjugates 1, 4, 5, 7, 11 and 28 (based on RGD-containing cyclic peptidomimetics of the general formula I, see Example 1), as well as conjugate 41 (based on an RGD-containing cyclic peptidomimetic of the general formula II, see Example 2), and the $IC_{50}$ values measured for these conjugates are presented in Table 10.

As shown, conjugates 1, 7, 28 and 41 showed the lowest $IC_{50}$ ($10^{-4}$ M), i.e., the highest biological activity; the $IC_{50}$ of conjugate 4 was slightly higher ($3\times10^{-4}$ M); and the $IC_{50}$ of conjugates 5 and 11 was the highest ($3\times10^{-3}$ M).

TABLE 10

The competitive binding level ($IC_{50}$) of various BTA-conjugates of the present invention to human $\alpha_v\beta_3$ integrin

| Conjugate | $IC_{50}$ (M) to human $\alpha_v\beta_3$ integrin |
|---|---|
| 1 | $10^{-4}$ |
| 4 | $3 \times 10^{-4}$ |
| 5 | $3 \times 10^{-3}$ |
| 7 | $10^{-4}$ |
| 11 | $3 \times 10^{-3}$ |
| 28 | $10^{-4}$ |
| 41 | $10^{-4}$ |

* The characterization of each one of the conjugates 1, 4, 5, 7, 11 and 28, and of conjugate 41, is presented in Table 1 and Table 2, respectively, hereinbefore.

Example 11

Conjugates 1, 4 and 41 Accumulate in the Necrotic Core of MDA Necrotic Tumors In this study, the specific accumulation pattern of conjugates 1, 4 and 41 in orthotopic primary lesions of mammary carcinoma model, monitored by fluorescence signal generated by the tumor, and the fluorescence signal generated by these conjugates were examined. The localization of the conjugates in the tumors as time progress was also determined. Animals were treated as described in Materials and Methods, and fluorscence of both tumor cells and conjugates 1, 4 and 41 was monitored by IVIS® 100 imaging system from day 1 to 7.

Figure 1B:
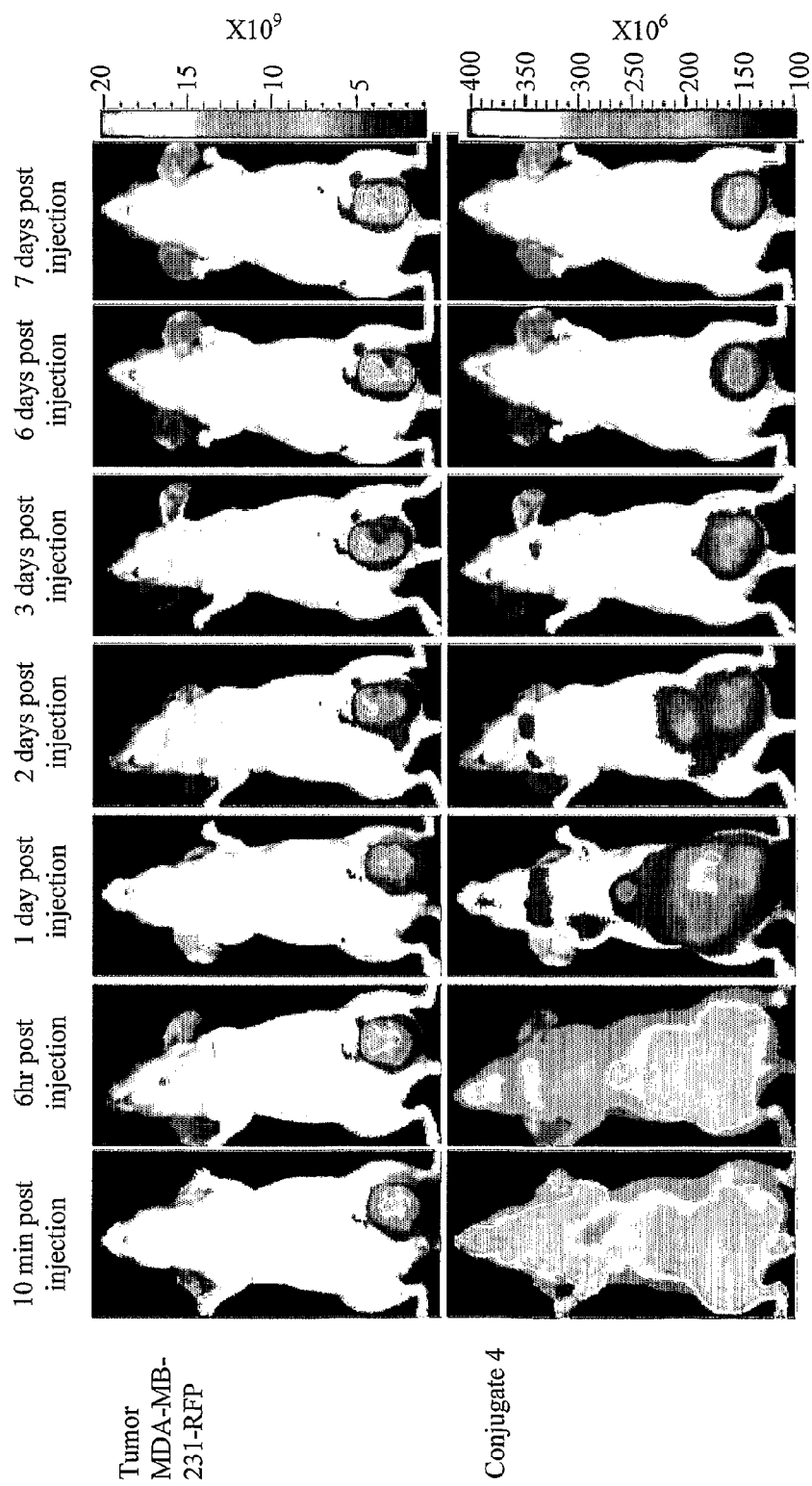
Figure 1C:
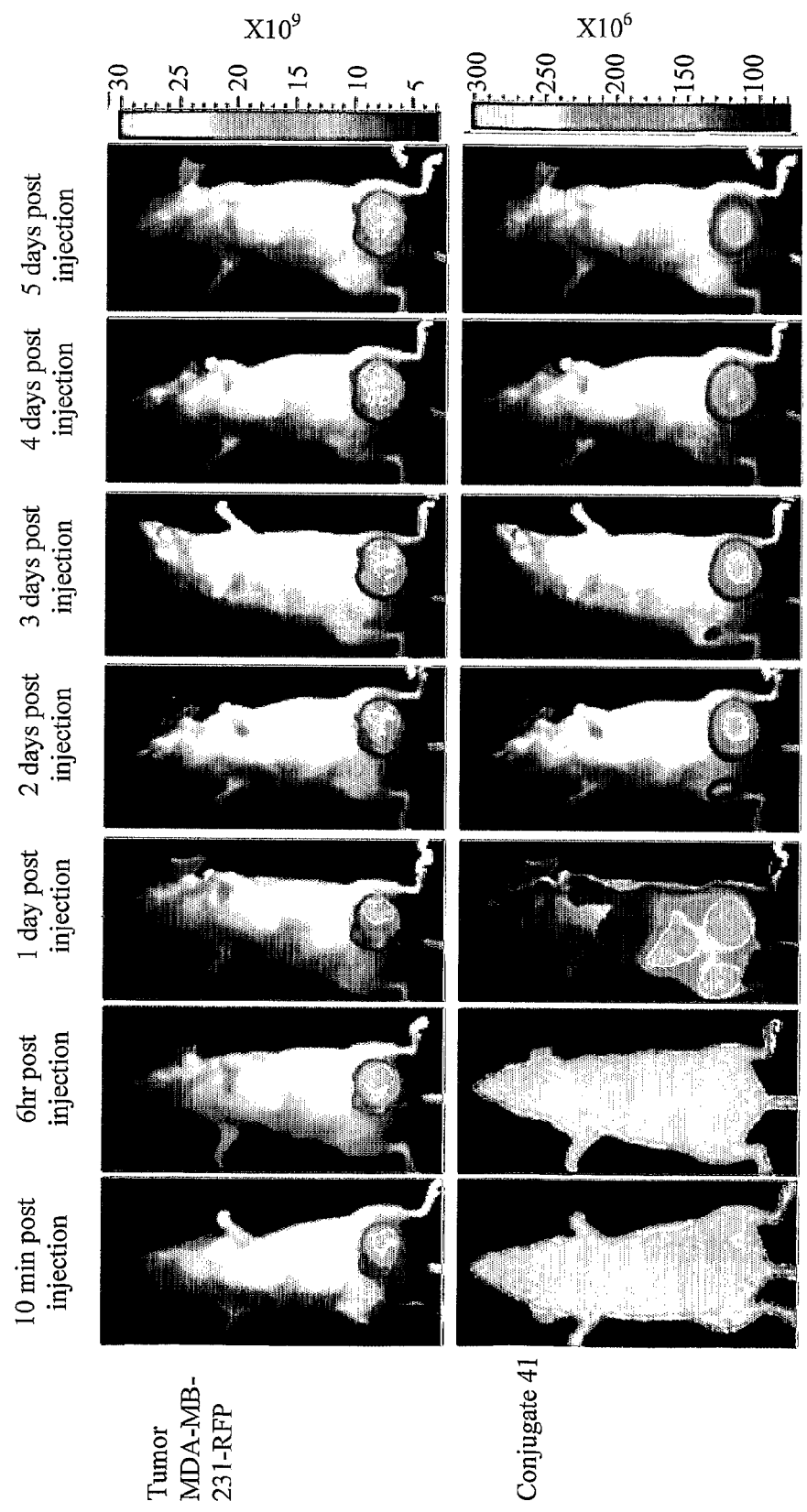

FIGS. 1A, 1B and 1C show the accumulation patterns of conjugates 1, 4 and 41, respectively, in orthotopic human breast MDA-MB-231-RFP primary large tumor in the mammary pad of CD-1 nude female mice, using the Xenogen IVIS® System. Whole animal images° were recorded concomitantly using filter sets comprising excitation filter 500-550 nm and emission filter 575-650 nm. Background filter set for subtraction the tissue auto fluorescence: excitation filter 460-490 nm and emission filter 575-650 nm. Photosensitizer imaging main filter set: excitation filter 665-695 nm, emission filter 810-875 nm.

Figure 2A:
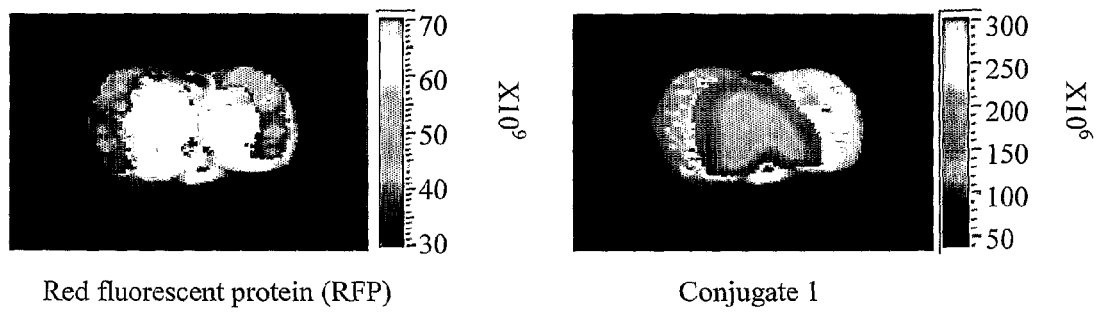
FIGS. 2A-2C show the accumulation of conjugates 1, 4 and 41 (2A, 2B and 2C, respectively) in the necrotic area of the breast cancer tumor. Mice were treated as described in Materials and Methods, and the fluorescence was monitored six days post injection using the Xenograph IVIS® system (color scale in units of photon/sec/cm²/steradian). As shown, the necrotic area in the central part of the tumor abolishes red fluorescence (left panel) but shows amassing of the conjugate (right panel).
Figure 2B:
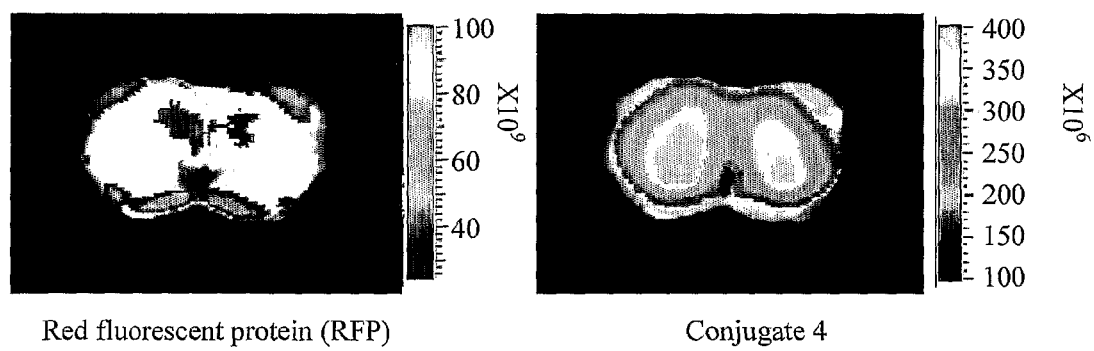
Figure 2C:
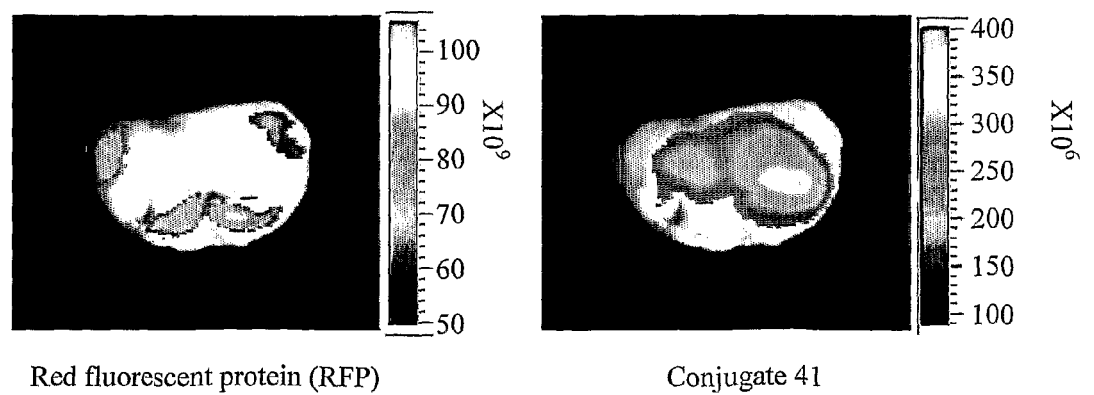

All conjugates accumulated in the tumor while completely clearing from the liver, providing a selective tumor imaging at ≥3 days to the end of the follow up period at 7 days post injection and an extremely slow clearance thereafter. Tumor size and location did not change throughout the experiment as seen by the red in vivo whole body images. As shown in FIGS. 2A, 2B and 2C, the localization of these conjugates six days post injection is in the necrotic area of the tumor.

Example 12

The Biological Activity of Conjugates 1, 4 and 41 on Prostate Cancer Cells

In this study, the biological activity of conjugates 1, 4 and 41 on LNCaP prostate cancer cells expressing $\alpha_v\beta_3$ integrin was examined. As shown above, these specific conjugates showed activity on ovarian carcinoma, colon carcinoma and breast cancer cells.

Figure 3A:
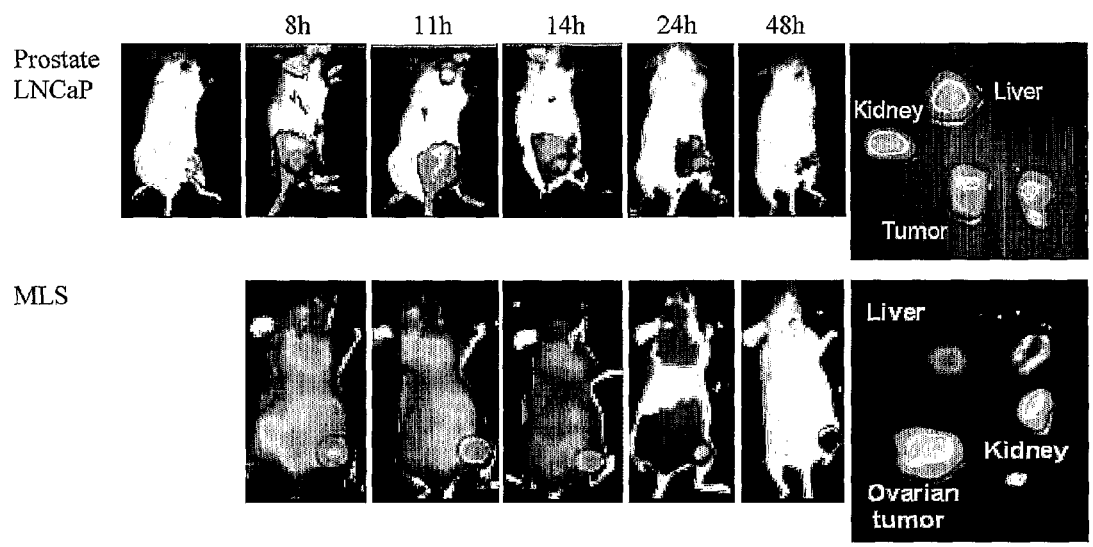
FIGS. 3A-3C show the accumulation of conjugates 1, 4 and 41 (3A, 3B and 3C, respectively) in LNCaP prostate cancer tumor compared with MLS ovarian tumor. Mice were treated as described in Materials and Methods, and the accumulation of the conjugate in the implanted tumor was monitored at certain points in time (8, 11, 14, 24 and 48 hrs for conjugate 1; 8, 14, 24 and 48 hrs for conjugate 4; and 8, 12 and 24 hrs for conjugate 41) post injection using the Xenograph IVIS® system. The accumulation profiles of the conjugates in prostate (upper panel) and ovarian (lower panel) tumors were nearly the same, wherein in both cases, the highest fluorescent level was observed at 8-11 (conjugate 1), 8-14 (conjugate 4) or 8-12 (conjugate 41) hrs after injection and the conjugate stayed in the tumor up to 48 hrs in the case of conjugates 1 and 4, or 24 hrs in the case of conjugate 41. The arrow in the upper left picture shows the place of the prostate tumor. The right picture in each panel shows the excited organs 14 hrs after injection, wherein the high fluorescent level observed in the liver and kidney suggests the clearance of the conjugate through these organs.
Figure 3B:
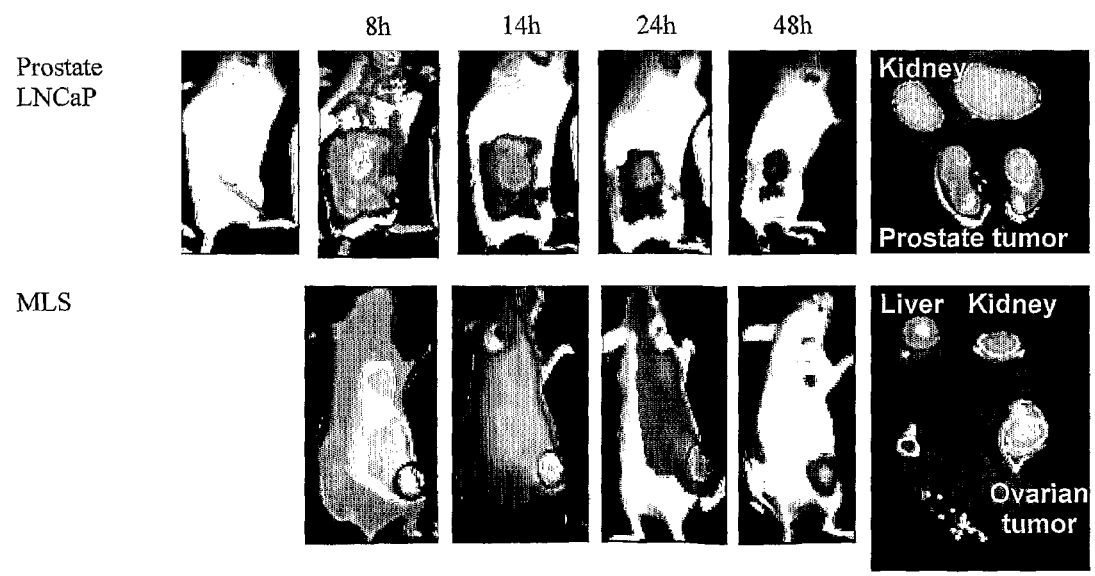
Figure 3C:
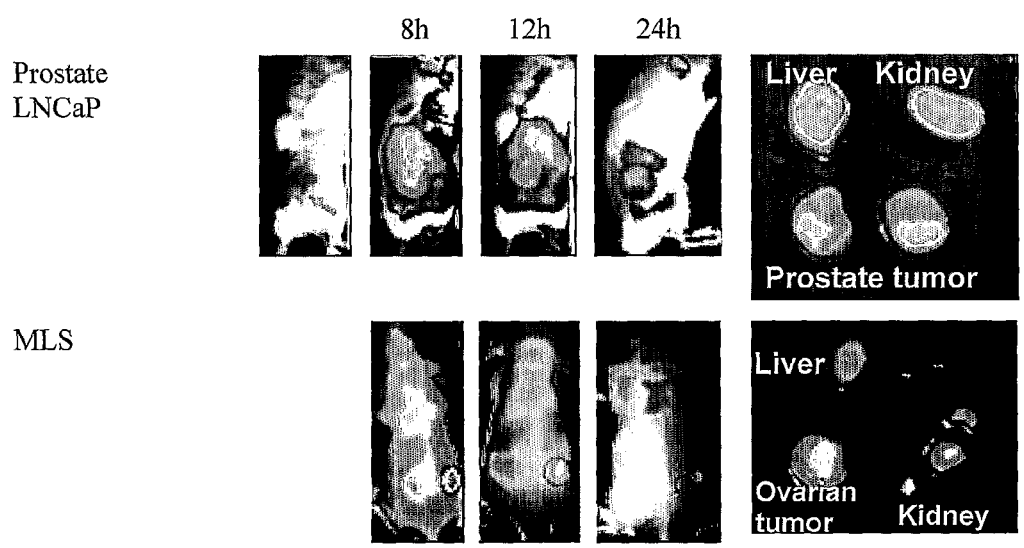

The accumulation of the conjugates in the implanted tumor was monitored at 8, 11, 14, 24 and 48 hrs post injection using the Xenograph IVIS® system, and as shown in FIGS. 3A, 3B and 3C, referring to conjugates 1, 4 and 41, respectively, the highest fluorescent level was observed in tumor area at 8 to 11-14 hrs after injection, and the conjugate stayed in the tumor for up to 48 hrs in the cases of conjugates 1 and 4, and up to 24 hrs in the case of conjugate 41. As further shown, the accumulation profiles of these conjugates in prostate and ovarian tumors were nearly the same.

Example 13

The Toxicity of Conjugates 1, 4 and 41 on Rats

Toxicity study of conjugates 1, 4 and 41 was performed on Wistar rats (5 females, 170-190 g, and 5 males, 288-315 g). The various conjugates at dose of 50 mg/kg were injected into the tail vein during 1-2 min. Animals were survived and did not show any behavior or motility problems. After five days, no evidence of necrosis or inflammation was found in the liver or the kidneys of these animals, suggesting that these conjugates are not toxic at the tested dose.

Scheme 2: The chemical structures of the various payload moieties used, linked to the cyclic peptidomimetic (marked a "Peptide") of the present invention

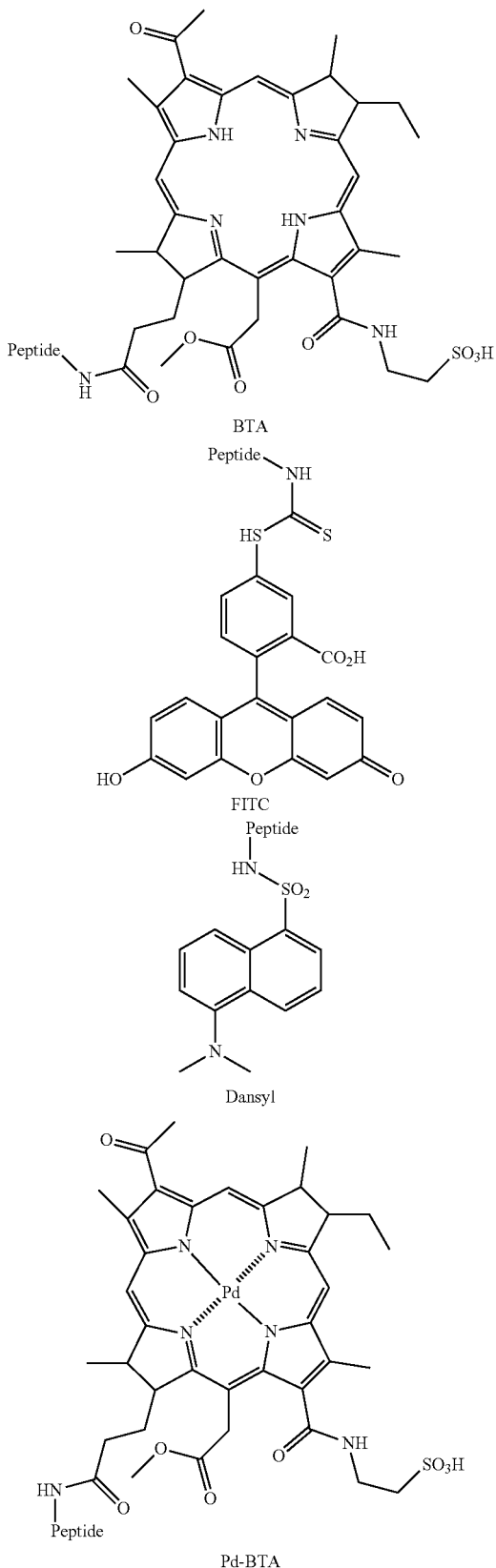

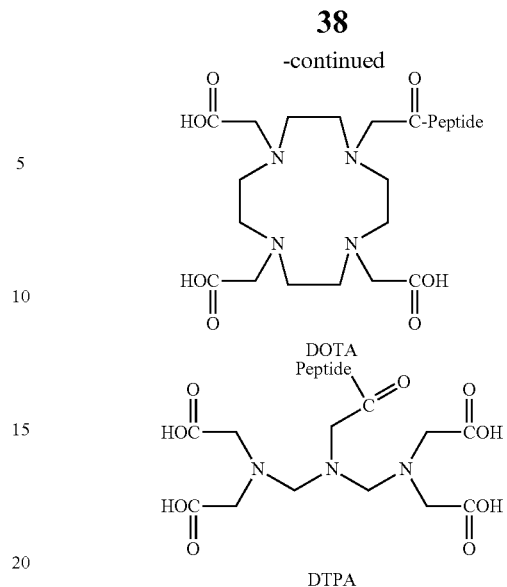

REFERENCES

Arap W., Haedicke W., Bernasconi M., Kain R., Rajotte D., Krajewski S., Ellerby H. M., Bredesen D. E., Pasqualini R., Ruoslahti E., *Proc. Natl. Acad. Sci. U.S.A.*, 2002, 99, 1527-1531

Arap W., Pasqualini R., Ruoslahti E., *Science*, 1998, 279, 377-380

Assa-Munt N., Jia X., Laakkonen P., Ruoslahti E., *Biochemistry*, 2001, 40, 2373-2378

Banfi, L. Basso A., Damonte G., De Pellegrini F., Galatini A., Guanti G., Monfardini I., Riva R., Scapolla C., *Bioorganic & Medicinal Chemistry Letters*, 2007, 17, 1341-1345

Belvisi L., Riccioni T., Marcellini M., Vesci L., Chiarucci I., Efrati D., Potenza D., Scolastico C., Manzoni L., Lombardo K., Stasi M. A., Orlandi A., Ciucci A., Nico B., Ribatti D., Giannini G., Presta M., Carminati P., Pisano C., *Mol. Cancer Ther.*, 2005, 4, 11

Chaleix V., Sol V., Huang Y. M., Guilloton M., Granet R., Blais J. C., Krausz P., *Eur. J Org. Chem.*, 2003, 1486-1493

Dijkgraaf I., Kruijtzer J. A. W., Frielink C., Soede A. C., Hilbers H. W., Oyen W. J. G., Corstens F. H. M., Liskamp R. M. J., Boerman O. C., *Nuclear Medicine and Biology*, 2006, 33, 953-961

D'Souza S. E., Ginsberg M. H., Plow E. F., *Trends Biochem. Sci.*, 1991, 16, 246-250

Ellerby H. M., Arap W., Ellerby L. M., Kain R., Andrusiak R., Del Rio G., Krajewski S., Rao R., Ruoslahti E., Bredesen D. E., Pasqualini R., *Nat. Med.*, 1999, 5, 1032-1038

Goligorsky M. S., Kessler H., Romanov V. I., *Nephrol. Dial. Transplant.*, 1998, 13, 254-263

Hardan I., Weiss L., Hershkovitz R., Greenspoon N., Alon R., Cahalon L., Reich S., Slavin S., Lider O., *Int. J. Cancer*, 1993, 55, 1023-1028

Haubner R., Gratias R., Diefenbach B., Goodman S. L., Jonczyk A., Kessler H., *J. Am. Chem. Soc.*, 1996, 118, 7461-7472

Haubner R., Wester H. J., Weber W. A., Mang C., Ziegler S. L., Goodman S. L., Senekowitsch-Schmidtke R., Kessler H., Schwaiger M., *Cancer res.*, 2001, 61, 1781-1785

Joshi P., Chung C. Y., Aukhil I., Erickson H. P., *J. Cell Sci.*, 1993, 106, 389-400

Kawaguchi M., Hosotani R., Ohishi S., Fujii N., Tulachan S. S., Koizumi M., Toyoda E., Masui T., Nakajima S., Tsuji S., Ida J., Fujimoto K., Wada M., Doi R., Imamura M., *Biochem. Biophys. res. com.,* 2001, 288, 711-717

Koivunen E., Wang B., Dickinson C. D., Ruoslahti E., *Methods Enzymol.,* 1994, 245, 346-369

Lark M. W., Stroup G. B., Hwang S. M., James I. E., Rieman D. J., Drake F. H., Bradbeer J. N., Mathur A., Erhard K. F., Newlander K. A., Ross S. T., Salyers K. L., Smith B. R, Miller W. H., Huffman W. F., Gowen M., *JPET,* 1999, 291, 612-617

Locardi E., Mullen D. G., Mattern R., Goodman M., *J. Peptide Sci.,* 1999, 5, 491-506

Pasqualini R., Ruoslahti E., *Nature,* 1996, 380, 364-366

Pasqualini R., Koivunen E., Ruoslahti E., *Nat. Biotechnol.,* 1997, 15, 542-546

Pasqualini R., Koivunen E., Kain R., Landenranta J., Sakamoto M., Stryhn A., Ashmun R. H., Shapiro L. H., Arap W., Rouslahti E., *Cancer res.,* 2000, 60, 722-727

Pierschbacher M., Ruoslahti E., *Nature,* 1984, 309, 30-33

Pierschbacher M. D., Rouslahti E., *J. Biol. Chem.,* 1987, 262, 17294-17298

Raboisson P., Manthey C. L., Chaikin M., Lattanze J., Crysler C., Leonard K., Pan W., Tomczuk B. E., Marugán J. J., *Eur. J. Med. Chem.,* 2006, 41, 847-861

Romanov V. I., Goligorsky M. S., *The prostate,* 1999, 39, 108-118

Ruoslahti E., *Annual Rev. Cell Dev. Biol.,* 1996, 12, 697-715

Ruoslahti E., *Seminars in cancer biology,* 2000, 10, 435-442

Ruoslahti E., *DDT,* 2002, 7, 1138-1143

Ruoslahti E., Pierschbacher M. D., *Science,* 1987, 238, 4826, 491-497

Ruoslahti E., Rajotte D., *Annu. Rev. Immunol.,* 2000, 18, 813-827

Saiki I., Murata J., Iida J., Sakurai T., Nishi N., Matsuno K., Azuma I., *Br. J. Cancer,* 1989, 60, 722-728

Su Z. F., Liu G., Gupta S., Zhu Z., Rusckowski M., Hnatowich D. J., *Bioconjug. Chem.,* 2002, 13, 561-570 van Hagen P. M., Breeman W. A., Bernard H. F., Schaar M., Mooij C. M., Srinivasan A., Schmidt M. A., Krenning E. P., de Jong M., *Int. J. Cancer,* 2000, 90, 186-198

The invention claimed is:

1. An arginine-glycine-aspartic acid (RGD)-containing cyclic peptidomimetic of the general formula I:

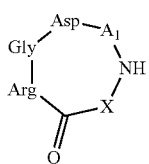

I wherein
the arginine residue is linked via its α-amino group to the backbone C=O;
X is —NH—R—, —O—R— or —S—R—, wherein R is a hydrocarbylene derived from ethane, ethene or cyclopropane; and
$A_1$ is an amino acid residue bearing an amino group on its side chain, linked via its carboxyl group to the backbone NH and via its side chain amino group to the α-carboxyl group of the aspartic acid residue, said amino acid is selected from the group consisting of diaminopropionic acid (Dap), ornithine (Orn) and lysine (Lys).

2. The RGD-containing cyclic peptidomimetic of claim 1, wherein:
X is —NH—R—, —O—R— or —S—R—, and R is a hydrocarbylene derived from ethane.

3. The RGD-containing cyclic peptidomimetic of claim 1, wherein:
(i) X is —NH—R—, R is a hydrocarbylene derived from ethane, and $A_1$ is Dap, Orn or Lys; or
(ii) X is —O—R—, R is a hydrocarbylene derived from ethane, and $A_1$ is Dap or Lys.

4. A conjugate of the RGD-containing cyclic peptidomimetic of claim 1 and a moiety of a payload selected from the group consisting of a fluorescent probe, a photosensitizer, a chelating agent and a cytotoxic agent, linked to the α-amino group of the amino acid residue $A_1$ in the peptidomimetic, optionally via a spacer.

5. The conjugate of claim 4, wherein said spacer is selected from the group consisting of a moiety of a natural or non-natural amino acid, a moiety of a small peptide having not more than 8 amino acids, a diamine residue, a $C_1$-$C_{25}$ hydrocarbylene and a soluble polymer.

6. The conjugate of claim 5, wherein said amino acid is selected from the group consisting of glycine (Gly), β-alanine (β-Ala), phenylalanine (Phe), D-phenylalanine (D-Phe), 1-naphthylalanine (1-Nal), D-1-naphthylalanine (D-1-Nal), γ-aminobutiric acid (GABA) and 3-(aminomethyl)benzoic acid; said diamine residue is —HN—$(CH_2)_2$—NH— or —HN—$(CH_2)_4$—NH—; said $C_1$-$C_{25}$ hydrocarbylene is a $C_1$-$C_{10}$ alkylene or phenylene, substituted by two end functional groups selected from the group consisting of OH, COOH, $SO_3H$, COSH and $NH_2$, thus forming ether, ester, amide, thioamide or sulfonamide groups; and said soluble polymer is selected from the group consisting of linear or branched polyethylene glycol (PEG) or copolymers thereof, polylactide (PLA) or copolymers thereof, polyesters having functional groups based on PLA, polyglycolide (PGA), polycaprolactone (PCL) or their copolymers and polyamides based on polymethacrylamide or their copolymers, said polymers having functional groups.

7. The conjugate of claim 4, wherein said fluorescent probe is BPheide taurine amide (BTA), fluorenyl isothiocyanate (FITC), dansyl, rhodamine, eosin or erythrosine; said photosensitizer is a porphyrin, a chlorophyll or a bacteriochlorophyll; said chelating agent is DTPA or DOTA; and said cytotoxic agent is an anthracycline chemotherapeutic agent selected from the group consisting of doxorubicin, daunorubicin, epirubicin, idarubicin and mitoxantrone, a mitotic inhibitor, a topoisomerase I inhibitor, or a topoisomerase II inhibitor.

8. The conjugate of claim 7, wherein:
(i) the payload is BTA, linked directly to $A_1$, X is —NH—R—, R is a hydrocarbylene derived from ethane, and $A_1$ is Dap, Orn, or Lys, herein identified conjugates 1, 4, and 5 respectively;
(ii) the payload is dansyl, linked directly to $A_1$, X is —NH—R—, R is a hydrocarbylene derived from ethane, and $A_1$ is Dap, Orn or Lys, herein identified conjugates 19, 18, and 16, respectively;
(iii) the payload is BTA, linked directly to $A_1$, X is —O—R—, R is a hydrocarbylene derived from ethane, and $A_1$ is Dap or Lys, herein identified conjugates 7 and 8, respectively;
(iv) the payload is BTA, linked via a spacer to $A_1$, X is —NH—R—, R is a hydrocarbylene derived from ethane, $A_1$ is Dap, and the spacer is a moiety of GABA or D-Phe, or a residue of 1,4-diaminobutane, herein identified conjugates 11, 28, and 33, respectively;
(v) the payload is FITC, linked via a spacer to $A_1$, X is —NH—R—, R is a hydrocarbylene derived from ethane, and:
(a) $A_1$ is Dap, and the spacer is a β-Ala moiety, herein identified conjugate 12; or
(b) $A_1$ is Lys, and the spacer is a moiety of β-Ala or GABA, herein identified conjugates 13 and 14, respectively;
(vi) the payload is dansyl, linked via a spacer to $A_1$, X is —NH—R—, R is a hydrocarbylene derived from ethane, $A_1$ is Dap or Lys, and the spacer is a Gly moiety, herein identified conjugates 20 and 17, respectively;
(vii) the payload is the bacteriochlorophyll derivative Pd-BTA, linked directly to $A_1$, X is —NH—R—, R is a hydrocarbylene derived from ethane, and $A_1$ is Dap, herein identified conjugate 34;
(viii) the payload is DTPA or DOTA, linked directly to $A_1$, X is —NH—R—, R is a hydrocarbylene derived from ethane, and $A_1$ is Dap, herein identified conjugates 35 and 36, respectively
(ix) the payload is a substituted BTA in which the taurine residue is replaced by —NH—$(CH_2)_2$—$NH_2$, said substituted BTA is linked directly to $A_1$, X is —NH—R—, R is a hydrocarbylene derived from ethane, and $A_1$ is Dap or Orn, herein identified conjugates 37 and 39, respectively; or (x) the payload is a substituted BTA in which the taurine residue is replace by —NH—$(CH_2)_2$—NH—$CH_3$, said substituted BTA is linked directly to $A_1$, X is —NH—R—, R is a hydrocarbylene derived from ethane, and $A_1$ is Dap or Orn, herein identified conjugates 38 and 40, respectively.

9. A pharmaceutical composition comprising a conjugate as defined in claim 4, or a pharmaceutical acceptable salt thereof, and a pharmaceutically acceptable carrier.

10. The pharmaceutical composition of claim 9, wherein the payload is a fluorescent probe; a photosensitizer; a chelating agent; or a cytotoxic agent.

11. The pharmaceutical composition of claim 10, wherein:
(i) the payload is a fluorescent probe, and the composition comprises a conjugate selected from the group consisting of the herein identified conjugates 1, 4, 5, 7, 8, 11-14, 16-20, 28 and 33;
(ii) the payload is a photosensitizer, and the composition comprises a conjugate selected from the group consisting of the herein identified conjugates 34 and 37-40; or
(iii) the payload is a chelating agent, and the composition comprises the herein identified conjugate 35 or 36.

12. The pharmaceutical composition of claim 10, wherein:
(i) the payload is a fluorescent probe, for diagnostic purposes;
(ii) the payload is a photosensitizer, for photodynamic therapy (PDT);
(iii) the payload is a chelating agent, for use in radio imaging or radiotherapy; or
(iv) the payload is a cytotoxic agent, for use in targeted chemotherapy.

13. The pharmaceutical composition of claim 12:
(i) consisting of the pharmaceutical composition of 80(i), for visualization of organs and tissues, or for diagnosis of tumors; or
(ii) consisting of the pharmaceutical composition of 80(ii), for PDT of tumors or nonneoplastic tissue.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (1)..(4)
<223> OTHER INFORMATION: Xaa is linked through its alpha- or side chain
      carboxyl group to Arg via a -NH-X-CO- group, wherein X is as
      defined in the description.
<220> FEATURE:
<221> NAME/KEY: MISC_FEATURE
<222> LOCATION: (4)..(4)
<223> OTHER INFORMATION: Xaa is Lys, diaminopropionic acid (Dap),
      diaminobutyric acid (Dab), Orn, Glu, Asp or aminoadipic acid.

<400> SEQUENCE: 1

Arg Gly Asp Xaa
1

<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(6)
<223> OTHER INFORMATION: Xaa at position 6 is linked through its alpha-
      amino group to the Xaa at position 1 via a -CO- group
<220> FEATURE:
<221> NAME/KEY: MISC_FEATURE
<222> LOCATION: (1)..(1)
<223> OTHER INFORMATION: Xaa is Lys, diaminopropionic acid (Dap),
      diaminobutyric acid (Dab), Orn, Glu, Asp or aminoadipic acid
<220> FEATURE:
<221> NAME/KEY: MISC_FEATURE
<222> LOCATION: (5)..(5)
<223> OTHER INFORMATION: Xaa is diaminopropionic acid (Dap),
      daiminobutyric acid (Dab), Orn or Lys, amidated at its C-terminus
<220> FEATURE:
<221> NAME/KEY: MISC_FEATURE
<222> LOCATION: (6)..(6)
```

```
<223> OTHER INFORMATION: Xaa is Phe, D-Phe, Val, Gly or Asp

<400> SEQUENCE: 2

Xaa Arg Gly Asp Xaa Xaa
1               5
```